(12) United States Patent
Morman et al.

(10) Patent No.: US 7,651,653 B2
(45) Date of Patent: Jan. 26, 2010

(54) MACHINE AND CROSS-MACHINE DIRECTION ELASTIC MATERIALS AND METHODS OF MAKING SAME

(75) Inventors: Michael T. Morman, Knoxville, TN (US); Paul Theodore Van Gompel, Hortonville, WI (US); Jennifer Marvin, Greenville, WI (US); Thomas Harold Roessler, Appleton, WI (US); James M. Carr, Kaukauna, WI (US); Yung Hsiang Huang, Appleton, WI (US); Mary Jo Meyer, Neenah, WI (US); Eric Donald Johnson, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 714 days.

(21) Appl. No.: 11/020,970

(22) Filed: Dec. 22, 2004

(65) Prior Publication Data

US 2006/0131783 A1 Jun. 22, 2006

(51) Int. Cl.
*B29C 55/08* (2006.01)
*D04H 1/00* (2006.01)
*D04H 3/00* (2006.01)

(52) U.S. Cl. ............ 264/290.2; 264/239; 264/241; 264/257; 264/280; 264/288.4; 442/328

(58) Field of Classification Search .......... 264/288.4, 264/290.2
See application file for complete search history.

(56) References Cited

U.S. PATENT DOCUMENTS 3,338,992 A   8/1967   Kinney
3,341,394 A   9/1967   Kinney
3,502,538 A   3/1970   Petersen
3,502,763 A   3/1970   Hartmann
3,542,615 A   11/1970  Dobo et al.
3,692,618 A   9/1972   Dorschner et al.
3,708,831 A   1/1973   Burger
3,802,817 A   4/1974   Matsuki et al.
3,849,241 A   11/1974  Butin et al.
3,904,465 A   9/1975   Haase et al.
3,949,128 A   4/1976   Ostermeier
4,039,364 A   8/1977   Rasmussen
4,100,324 A   7/1978   Anderson et al.

(Continued)

FOREIGN PATENT DOCUMENTS

EP   0030418 A1   6/1981

(Continued)

OTHER PUBLICATIONS

ASTM Designation: D1388-96, "Standard Test Method for Stiffness of Fabrics", Jun. 1996, pp. 313-318.

*Primary Examiner*—Joseph S. Del Sole
*Assistant Examiner*—Magali P Théodore
(74) *Attorney, Agent, or Firm*—Steven D. Flack; Richard M. Shane

(57) ABSTRACT

A method for producing a machine direction and cross-machine direction elastic laminate includes the steps of providing a one direction elastic laminate material including at least one elastic layer and one facing layer and having a single direction of elasticity and coursing the one direction elastic laminate material through at least one stretching apparatus, such that the stretching apparatus stretches the laminate material in a direction perpendicular to the single direction of elasticity of the elastic laminate material, thereby producing a material that extends in a direction perpendicular to the direction of elasticity and also extends the elastic performance of the laminate in the single direction of elasticity.

21 Claims, 5 Drawing Sheets

U.S. PATENT DOCUMENTS

| | | |
|---|---|---|
| 4,105,491 A | 8/1978 | Haase et al. |
| 4,107,364 A | 8/1978 | Sisson |
| 4,111,733 A | 9/1978 | Periers |
| 4,116,892 A | 9/1978 | Schwarz |
| 4,144,008 A | 3/1979 | Schwarz |
| 4,151,245 A | 4/1979 | Suzuki |
| 4,153,664 A | 5/1979 | Sabee |
| 4,153,751 A | 5/1979 | Schwarz |
| 4,209,563 A | 6/1980 | Sisson |
| 4,223,059 A | 9/1980 | Schwarz |
| 4,238,443 A | 12/1980 | Levy |
| 4,251,585 A | 2/1981 | Schwarz |
| 4,285,100 A | 8/1981 | Schwarz |
| 4,332,035 A | 6/1982 | Mano |
| 4,340,563 A | 7/1982 | Appel et al. |
| 4,368,565 A | 1/1983 | Schwarz |
| 4,422,892 A | 12/1983 | Plant |
| 4,440,709 A * | 4/1984 | Rasmussen ................. 264/145 |
| 4,475,971 A | 10/1984 | Canterino |
| 4,517,714 A | 5/1985 | Sneed et al. |
| 4,525,407 A | 6/1985 | Ness |
| 4,554,207 A | 11/1985 | Lee |
| 4,568,723 A | 2/1986 | Lu |
| 4,578,307 A | 3/1986 | Niki et al. |
| 4,579,907 A | 4/1986 | Wildenau |
| 4,613,640 A | 9/1986 | Deisler et al. |
| 4,629,525 A * | 12/1986 | Rasmussen .................. 156/84 |
| 4,655,760 A * | 4/1987 | Morman et al. ........ 604/385.26 |
| 4,663,220 A | 5/1987 | Wisneski et al. |
| 4,668,752 A | 5/1987 | Tominari et al. |
| 4,680,213 A | 7/1987 | Fourezon |
| 4,687,477 A | 8/1987 | Suzuki |
| 4,704,116 A | 11/1987 | Enloe |
| 4,716,183 A | 12/1987 | Gamarra et al. |
| 4,720,415 A | 1/1988 | Vander Wielen et al. |
| 4,725,468 A | 2/1988 | McIntyre |
| 4,732,928 A | 3/1988 | Mizushiro et al. |
| 4,741,949 A | 5/1988 | Morman et al. |
| 4,756,942 A | 7/1988 | Aichele |
| 4,761,198 A | 8/1988 | Salerno |
| 4,761,324 A | 8/1988 | Rautenberg et al. |
| 4,772,657 A | 9/1988 | Akiyama et al. |
| 4,789,699 A | 12/1988 | Keiffer et al. |
| 4,793,885 A | 12/1988 | Rasmussen |
| 4,795,668 A | 1/1989 | Krueger et al. |
| 4,798,603 A | 1/1989 | Meyer et al. |
| 4,798,853 A | 1/1989 | Handlin, Jr. |
| 4,801,482 A | 1/1989 | Goggans et al. |
| 4,804,577 A | 2/1989 | Hazelton et al. |
| 4,806,300 A | 2/1989 | Walton et al. |
| 4,834,741 A | 5/1989 | Sabee |
| 4,835,218 A | 5/1989 | Yoshimura et al. |
| 4,842,666 A | 6/1989 | Werenicz |
| 4,863,785 A | 9/1989 | Berman et al. |
| 4,866,128 A | 9/1989 | Gergen et al. |
| 4,880,420 A | 11/1989 | Pomparelli |
| 4,900,619 A | 2/1990 | Ostrowski et al. |
| 4,904,728 A | 2/1990 | George |
| 4,904,731 A | 2/1990 | Holden et al. |
| 4,906,507 A | 3/1990 | Grynaeus et al. |
| 4,908,247 A | 3/1990 | Baird et al. |
| 4,910,064 A | 3/1990 | Sabee |
| 4,921,643 A | 5/1990 | Walton et al. |
| 4,929,492 A | 5/1990 | Carey, Jr. |
| 4,965,122 A | 10/1990 | Morman |
| 4,968,313 A | 11/1990 | Sabee |
| 4,968,754 A | 11/1990 | Wong |
| 4,970,259 A | 11/1990 | Mitchell et al. |
| 4,977,011 A | 12/1990 | Smith |
| 4,977,014 A | 12/1990 | Mitchell et al. |
| 4,978,719 A | 12/1990 | Wong |
| 4,978,721 A | 12/1990 | Wong |
| 4,981,747 A | 1/1991 | Morman |
| 4,984,584 A | 1/1991 | Hansen et al. |
| 4,988,770 A | 1/1991 | Wong |
| 4,992,124 A | 2/1991 | Kurihara et al. |
| 4,995,928 A | 2/1991 | Sabee |
| 5,002,815 A | 3/1991 | Yamanaka et al. |
| 5,011,719 A | 4/1991 | Gehrke et al. |
| 5,015,695 A | 5/1991 | Wong |
| 5,026,798 A | 6/1991 | Canich et al. |
| 5,028,289 A | 7/1991 | Rasmussen |
| 5,043,036 A | 8/1991 | Swenson |
| 5,057,368 A | 10/1991 | Largman et al. |
| 5,064,802 A | 11/1991 | Stevens et al. |
| 5,068,138 A | 11/1991 | Mitchell et al. |
| 5,069,970 A | 12/1991 | Largman et al. |
| 5,073,436 A | 12/1991 | Antonacci et al. |
| 5,085,655 A | 2/1992 | Mann et al. |
| 5,091,471 A | 2/1992 | Graves et al. |
| 5,093,422 A | 3/1992 | Himes |
| 5,108,820 A | 4/1992 | Kaneko et al. |
| 5,114,781 A | 5/1992 | Morman |
| 5,116,662 A | 5/1992 | Morman |
| 5,117,540 A | 6/1992 | Walton et al. |
| 5,139,831 A | 8/1992 | Mueller |
| 5,143,679 A | 9/1992 | Weber et al. |
| 5,143,968 A | 9/1992 | Diehl et al. |
| 5,156,793 A | 10/1992 | Buell et al. |
| 5,167,897 A | 12/1992 | Weber et al. |
| 5,175,210 A | 12/1992 | Machado |
| 5,176,668 A | 1/1993 | Bernardin |
| 5,176,672 A | 1/1993 | Bruemmer et al. |
| 5,186,779 A | 2/1993 | Tubbs |
| 5,192,606 A | 3/1993 | Proxmire et al. |
| 5,198,281 A | 3/1993 | Muzzy et al. |
| 5,200,246 A | 4/1993 | Sabee |
| 5,206,300 A | 4/1993 | Chamberlain |
| 5,209,801 A | 5/1993 | Smith |
| 5,210,147 A | 5/1993 | Southwick |
| 5,219,633 A | 6/1993 | Sabee |
| 5,226,992 A * | 7/1993 | Morman .................... 156/62.4 |
| 5,229,191 A | 7/1993 | Austin |
| 5,230,701 A | 7/1993 | Meyer et al. |
| 5,232,777 A | 8/1993 | Sipinen et al. |
| 5,236,770 A | 8/1993 | Assent et al. |
| 5,238,733 A | 8/1993 | Joseph et al. |
| 5,244,716 A | 9/1993 | Thornton et al. |
| 5,256,231 A | 10/1993 | Gorman et al. |
| 5,259,902 A | 11/1993 | Muckenfuhs |
| 5,266,394 A | 11/1993 | Diehl et al. |
| 5,272,236 A | 12/1993 | Lai et al. |
| 5,274,037 A | 12/1993 | Miller |
| 5,277,976 A | 1/1994 | Hogle et al. |
| 5,278,220 A | 1/1994 | Vermeire et al. |
| 5,278,272 A | 1/1994 | Lai et al. |
| 5,292,795 A | 3/1994 | Southwick et al. |
| 5,296,289 A | 3/1994 | Collins |
| 5,304,599 A | 4/1994 | Himes |
| 5,312,500 A | 5/1994 | Kurihara et al. |
| 5,320,899 A | 6/1994 | Djiauw |
| 5,322,728 A | 6/1994 | Davey et al. |
| 5,330,829 A | 7/1994 | Miller |
| 5,334,437 A | 8/1994 | Zafiroglu |
| 5,334,446 A | 8/1994 | Quantrille et al. |
| 5,336,545 A | 8/1994 | Morman |
| 5,336,552 A | 8/1994 | Strack et al. |
| 5,336,708 A | 8/1994 | Chen |
| 5,340,840 A | 8/1994 | Park et al. |
| 5,342,469 A | 8/1994 | Bodford et al. |
| 5,344,691 A | 9/1994 | Hanschen et al. |
| 5,360,854 A | 11/1994 | Bozich, Jr. |
| 5,369,174 A | 11/1994 | Hasselbring |
| 5,374,696 A | 12/1994 | Rosen et al. |

| | | |
|---|---|---|
| 5,376,198 A | 12/1994 | Fahrenkrug et al. |
| 5,382,400 A | 1/1995 | Pike et al. |
| 5,385,775 A | 1/1995 | Wright |
| 5,391,607 A | 2/1995 | Fujii et al. |
| 5,393,599 A | 2/1995 | Quantrille et al. |
| 5,393,841 A | 2/1995 | Himes et al. |
| 5,399,219 A | 3/1995 | Roessler et al. |
| 5,407,507 A | 4/1995 | Ball |
| 5,413,849 A | 5/1995 | Austin et al. |
| 5,415,925 A | 5/1995 | Austin et al. |
| 5,418,045 A | 5/1995 | Pike et al. |
| 5,422,172 A | 6/1995 | Wu |
| 5,431,991 A | 7/1995 | Quantrille et al. |
| 5,447,462 A | 9/1995 | Smith et al. |
| 5,466,410 A | 11/1995 | Hills |
| 5,468,428 A | 11/1995 | Hanschen et al. |
| 5,470,639 A | 11/1995 | Gessner |
| 5,472,775 A | 12/1995 | Obijeski et al. |
| 5,476,563 A | 12/1995 | Nakata |
| 5,484,645 A | 1/1996 | Lickfield et al. |
| 5,486,166 A | 1/1996 | Bishop et al. |
| 5,486,574 A | 1/1996 | Himes et al. |
| 5,490,846 A | 2/1996 | Ellis et al. |
| 5,496,429 A | 3/1996 | Hasse et al. |
| 5,498,468 A | 3/1996 | Blaney |
| 5,501,679 A | 3/1996 | Krueger et al. |
| 5,509,915 A | 4/1996 | Hanson et al. |
| 5,518,801 A | 5/1996 | Chappell et al. |
| 5,523,146 A | 6/1996 | Bodford et al. |
| 5,529,830 A | 6/1996 | Dutta et al. |
| H1558 H | 7/1996 | Goulait et al. |
| 5,534,330 A | 7/1996 | Groshens |
| 5,540,796 A | 7/1996 | Fries |
| 5,547,531 A | 8/1996 | Allen et al. |
| 5,548,013 A | 8/1996 | Fujii et al. |
| 5,549,964 A | 8/1996 | Shohji et al. |
| 5,560,793 A | 10/1996 | Ruscher et al. |
| 5,567,760 A | 10/1996 | Walther et al. |
| 5,576,090 A | 11/1996 | Suzuki |
| 5,582,668 A | 12/1996 | Kling |
| 5,585,411 A | 12/1996 | Hwo |
| 5,591,792 A | 1/1997 | Hattori et al. |
| 5,592,690 A | 1/1997 | Wu |
| 5,595,618 A | 1/1997 | Fries et al. |
| 5,597,430 A | 1/1997 | Rasche |
| 5,609,702 A | 3/1997 | Andersen |
| 5,610,238 A | 3/1997 | Himes et al. |
| 5,615,460 A | 4/1997 | Weirich et al. |
| 5,620,545 A | 4/1997 | Braun et al. |
| 5,626,571 A | 5/1997 | Young et al. |
| 5,627,235 A | 5/1997 | Himes |
| 5,628,097 A | 5/1997 | Benson et al. |
| 5,628,741 A | 5/1997 | Buell et al. |
| 5,628,856 A | 5/1997 | Dobrin et al. |
| 5,633,286 A | 5/1997 | Chen |
| 5,639,831 A | 6/1997 | Himes et al. |
| 5,645,672 A | 7/1997 | Dobrin |
| 5,647,864 A | 7/1997 | Allen et al. |
| 5,652,041 A | 7/1997 | Buerger et al. |
| 5,660,664 A | 8/1997 | Herrmann |
| 5,665,822 A | 9/1997 | Bitler et al. |
| 5,681,302 A | 10/1997 | Melbye et al. |
| 5,683,787 A | 11/1997 | Boich et al. |
| 5,691,034 A | 11/1997 | Krueger et al. |
| 5,695,487 A | 12/1997 | Cohen et al. |
| 5,695,840 A | 12/1997 | Mueller |
| 5,714,257 A | 2/1998 | Shoh et al. |
| 5,719,226 A | 2/1998 | Kegley |
| 5,723,087 A | 3/1998 | Chappell et al. |
| 5,730,821 A | 3/1998 | Joest et al. |
| 5,733,635 A | 3/1998 | Terakawa et al. |
| 5,733,822 A | 3/1998 | Gessner et al. |
| 5,736,219 A | 4/1998 | Suehr et al. |
| 5,741,857 A | 4/1998 | Esneault et al. |
| 5,753,343 A | 5/1998 | Braun et al. |
| 5,756,580 A | 5/1998 | Natori et al. |
| 5,760,105 A | 6/1998 | Okada et al. |
| 5,766,737 A | 6/1998 | Willey et al. |
| 5,769,993 A | 6/1998 | Baldauf |
| 5,773,373 A | 6/1998 | Wynne et al. |
| 5,773,374 A | 6/1998 | Wood et al. |
| 5,777,028 A | 7/1998 | Okada et al. |
| 5,777,031 A | 7/1998 | Djiauw et al. |
| 5,777,043 A | 7/1998 | Shafer et al. |
| 5,789,046 A | 8/1998 | Mueller |
| 5,789,328 A | 8/1998 | Kurihara et al. |
| 5,804,011 A | 9/1998 | Dutta et al. |
| 5,804,286 A | 9/1998 | Quantrille et al. |
| 5,804,512 A | 9/1998 | Lickfield et al. |
| 5,804,628 A | 9/1998 | Busnel et al. |
| 5,814,176 A | 9/1998 | Proulx |
| 5,814,390 A | 9/1998 | Stokes et al. |
| 5,814,569 A | 9/1998 | Suzuki et al. |
| 5,840,632 A | 11/1998 | Miller |
| 5,840,633 A | 11/1998 | Kurihara et al. |
| 5,843,068 A | 12/1998 | Allen et al. |
| 5,847,051 A | 12/1998 | Hwo et al. |
| 5,861,074 A | 1/1999 | Wu |
| 5,863,978 A | 1/1999 | Vosters |
| 5,883,155 A | 3/1999 | Hoerner et al. |
| 5,884,639 A | 3/1999 | Chen |
| 5,885,686 A | 3/1999 | Cederblad et al. |
| 5,886,908 A | 3/1999 | Conn et al. |
| 5,888,607 A | 3/1999 | Seth et al. |
| 5,891,957 A | 4/1999 | Hansen et al. |
| 5,906,879 A | 5/1999 | Huntoon et al. |
| 5,914,084 A | 6/1999 | Benson et al. |
| 5,921,973 A | 7/1999 | Newkirk et al. |
| 5,932,648 A | 8/1999 | Troska et al. |
| 5,955,187 A | 9/1999 | McCormack et al. |
| 6,096,668 A | 8/2000 | Abuto et al. |
| 6,114,263 A | 9/2000 | Benson et al. |
| 6,149,637 A | 11/2000 | Allen et al. |
| 6,203,654 B1 | 3/2001 | McFall et al. |
| 6,210,388 B1 | 4/2001 | Widlund et al. |
| 6,214,274 B1 | 4/2001 | Melius et al. |
| 6,258,308 B1 | 7/2001 | Brady et al. |
| 6,264,864 B1 | 7/2001 | Mackay |
| 6,265,045 B1 | 7/2001 | Mushaben |
| 6,313,372 B1 | 11/2001 | Suzuki |
| 6,368,444 B1 | 4/2002 | Jameson et al. |
| 6,383,431 B1 | 5/2002 | Dobrin et al. |
| 6,403,505 B1 | 6/2002 | Groitzsch et al. |
| 6,481,483 B1 | 11/2002 | Kobayashi et al. |
| 6,570,056 B1 | 5/2003 | Tanzer et al. |
| 6,613,954 B1 | 9/2003 | Horney et al. |
| 6,702,801 B2 | 3/2004 | Van Gompel et al. |
| 7,078,089 B2 * | 7/2006 | Ellis et al. .................. 428/138 |
| 2001/0041487 A1 | 11/2001 | Brady et al. |
| 2001/0042938 A1 | 11/2001 | Mackay |
| 2002/0016122 A1 | 2/2002 | Curro et al. |
| 2002/0088534 A1 | 7/2002 | Kobayashi et al. |
| 2002/0089087 A1 | 7/2002 | Mushaben |
| 2002/0105110 A1 | 8/2002 | Dobrin et al. |
| 2003/0181120 A1 | 9/2003 | Wu et al. |
| 2004/0038085 A1 | 2/2004 | Litton et al. |
| 2004/0060649 A1 | 4/2004 | Van Gompel et al. |
| 2004/0087235 A1 | 5/2004 | Morman et al. |
| 2004/0118505 A1 | 6/2004 | Shimakawa et al. |
| 2004/0121687 A1 | 6/2004 | Morman et al. |
| 2004/0135286 A1 | 7/2004 | Ying et al. |
| 2004/0222553 A1 * | 11/2004 | Desai et al. ............ 264/171.24 |
| 2006/0003656 A1 | 1/2006 | Morman |

FOREIGN PATENT DOCUMENTS

| | | |
|---|---|---|
| EP | 0064853 B1 | 7/1986 |
| EP | 0090380 B1 | 12/1990 |
| EP | 0276100 B1 | 8/1994 |
| EP | 0575509 B1 | 10/1994 |
| EP | 0333212 B1 | 11/1994 |
| EP | 0379763 B1 | 12/1994 |
| EP | 0432763 B1 | 8/1995 |
| EP | 0370835 B1 | 12/1995 |
| EP | 0409315 B1 | 5/1997 |
| EP | 0573586 B1 | 5/1997 |
| EP | 0788874 A1 | 8/1997 |
| EP | 0803602 B1 | 10/1997 |
| EP | 0551327 B1 | 6/1998 |
| EP | 0582286 B1 | 10/1998 |
| EP | 0712304 B1 | 4/1999 |
| EP | 0782639 B1 | 10/1999 |
| EP | 0765146 B1 | 7/2000 |
| EP | 1069223 A1 | 1/2001 |
| EP | 0829566 B1 | 8/2001 |
| EP | 0977915 B1 | 10/2001 |
| EP | 1138472 A1 | 10/2001 |
| EP | 1151846 A2 | 11/2001 |
| EP | 1164007 A1 | 12/2001 |
| EP | 0852483 B1 | 4/2002 |
| EP | 0927096 B1 | 5/2002 |
| EP | 1047821 B1 | 5/2002 |
| EP | 1066962 B1 | 9/2004 |
| GB | 1521579 | 8/1978 |
| GB | 1526722 | 9/1978 |
| GB | 1526723 | 9/1978 |
| GB | 1526724 | 9/1978 |
| GB | 1553102 | 9/1979 |
| GB | 1579718 | 11/1980 |
| GB | 1598737 | 9/1981 |
| GB | 1598738 | 9/1981 |
| WO | WO 92/16371 | 10/1992 |
| WO | WO 95/04654 | 2/1995 |
| WO | WO 95/16425 | 6/1995 |
| WO | WO 96/10481 | 4/1996 |
| WO | WO 96/16216 | 5/1996 |
| WO | WO 98/04397 | 2/1998 |
| WO | WO 99/42068 | 8/1999 |
| WO | WO 00/19950 | 4/2000 |
| WO | WO 00/23255 | 4/2000 |
| WO | WO 00/23509 | 4/2000 |
| WO | WO 00/38918 | 7/2000 |
| WO | WO 00/46023 | 8/2000 |
| WO | WO 00/56522 | 9/2000 |
| WO | WO 00/69383 | 11/2000 |
| WO | WO 01/15645 | 3/2001 |
| WO | WO 01/23180 | 4/2001 |
| WO | WO 01/54900 | 8/2001 |
| WO | WO 01/88245 | 11/2001 |
| WO | WO 02/102592 | 12/2002 |
| WO | WO 03/000165 | 1/2003 |
| WO | WO 2004/020174 | 3/2004 |

* cited by examiner

FIG. 1
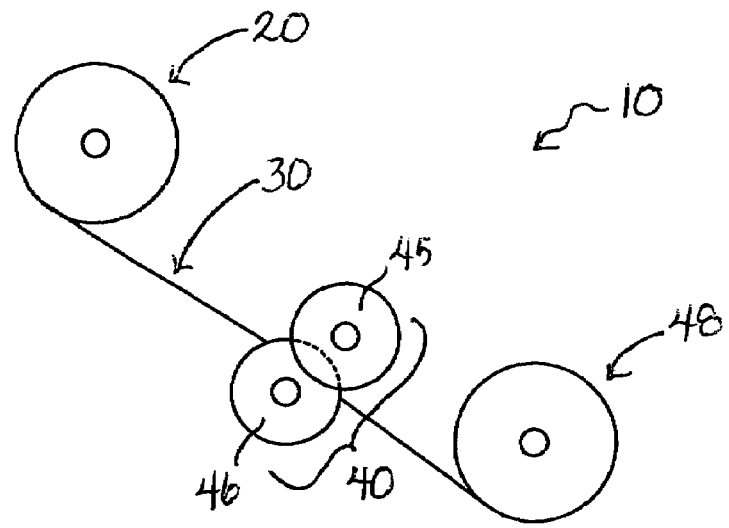
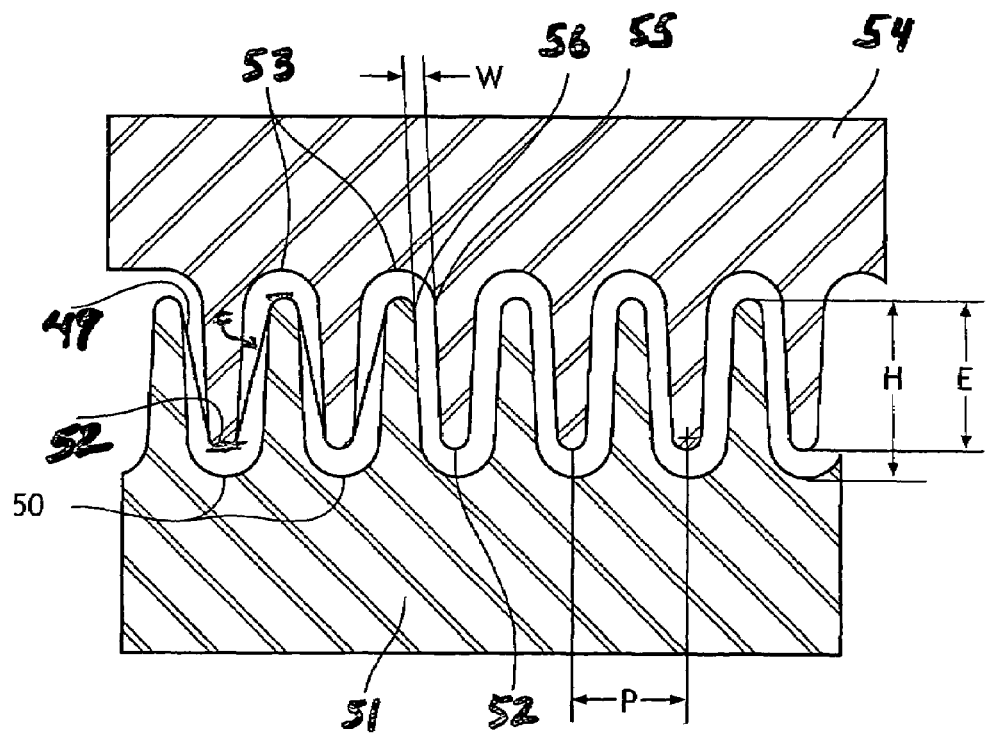
FIG. 2A

MACHINE AND CROSS-MACHINE DIRECTION ELASTIC MATERIALS AND METHODS OF MAKING SAME

FIELD OF INVENTION

The present invention relates to methods of making elastic clothlike laminates, including laminates made from neck bonded elastic materials and stretch bonded elastic materials. In particular, the present invention relates to methods of making multi-directional elastic laminates which can then be used at least as personal care product construction materials, such as bodyside facing liner material (or topsheets), outercovers (or backsheets), waist elastic materials, side panel elastic materials, leg cuff materials and elastic ear attachment materials. The present invention also relates to methods of manufacturing such materials.

BACKGROUND OF THE INVENTION

Polymeric films, elastic continuous filament arrays, nonwoven webs and laminates thereof may be manufactured into personal care products and components of products so inexpensively that the products could be viewed as disposable after only one or a few uses. Representatives of such products include articles such as diapers, adult incontinence devices, swimwear, feminine care products, and child training pants. Other such personal care disposable products include tissues, wipes, mattress pads, veterinary products, mortuary products, article covers and medical-related protective products such as everyday use garments and garments worn in a medical setting, face masks, sterilization wraps and hospital packaging materials.

It is generally known that the tactile properties of elastic materials can be improved by forming a laminate of the elastic material with one or more nonelastic materials on the outer surface(s) of the elastic material. For instance, in one such laminate material, a nonelastic material is joined to an elastic material while the elastic material is in a stretched condition so that when the elastic material is relaxed, the nonelastic material gathers between the locations where it is bonded to the elastic material. The resulting elastic laminate material is stretchable to the extent that the nonelastic material gathered between the bond locations allows the elastic material to elongate. In such a stretch bonded laminate process, either a just-formed (in-line produced material) or pre-formed (formed from a separately located manufacturing process) elastic material is stretched and then attached to the gatherable material. The elastic material is then allowed to retract, gathering the gatherable material and forming the stretch bonded laminate. An example of this type of stretch bonded laminate material is disclosed, for example, by U.S. Pat. No. 4,720,415 to Vander Wielen et al., U.S. Pat. No. 5,385,775 to Wright and Publication No. WO 01/88245, each of which is hereby incorporated by reference in its entirety. Such laminates may include an elastic layer of one or more film layers, one or more foam layers, one or more web layers (woven or nonwoven) or a combination of such, and at least one facing layer. While stretch bonded laminate materials are effective in providing high levels of stretch and recovery in the machine direction, it would be desirable to provide such formed material with stretch and recovery properties also in the cross-machine direction, i.e. direction perpendicular to the normal stretch and recovery direction of the elastic laminate. Further, it would be desirable to further enhance the stretch and recovery properties in the machine direction. Additionally, it would be desirable to enhance such properties in a single processing step.

It is also known to laminate (or bond) a necked material to an elastic sheet to produce a neck bonded laminate which is capable of stretch and recovery in the cross-machine direction. This process involves an elastic member being bonded to a non-elastic member while only the non-elastic member is extended in one direction (usually the machine direction) and necked in the transverse direction, so as to reduce its dimension in the direction orthogonal to the extension. Such is described in detail in U.S. Pat. Nos. 4,965,122, 4,981,747, 5,226,992, and 5,336,545 to Morman, each of which is incorporated by reference herein in its entirety. It would be desirable to provide a neck bonded laminate that has both cross-machine and machine direction stretch and recovery attributes, and that also has enhanced material properties. It would also be desirable to provide such enhanced material properties in one processing step.

It is further known to utilize intermeshing grooved rolls or discs on axle apparatus for stretching nonwoven webs. For instance, it is known to use grooved rolls generally to stretch a formed elastic and non-elastic (extendable) neck bonded laminate. See for example U.S. Publication 20040121687. For example, it is known to provide a laminate of an elastomer material and an extendable material (such as a nonwoven) and process the laminate through a grooved roll process to make either a cross-machine direction elastic material (using a grooved roll apparatus with machine direction oriented grooves), or a machine direction elastic material (using a grooved roll apparatus with cross-machine direction oriented grooves) or still alternatively, a machine direction and cross-machine direction elastic material (using a series of grooved roll apparatus with a first apparatus having machine direction oriented grooves followed by a grooved roll apparatus with cross-machine direction grooves or vice versa). However, it has proven difficult to make the machine direction/cross-machine direction elastic laminate because the extendable or gatherable material (nonwoven) has to be so highly extended, first in one direction and then in the perpendicular direction. There is therefore a need for elastic low cost laminates for use in personal care products (and methods for making such laminates) that demonstrate enhanced elastic performance (such as either reduced percent set upon a first stretch in use by a consumer, or increased elastic performance, or the combination) and that can also benefit from being produced via a single step processing arrangement. It is also a need to provide such material that is particularly soft to the touch and drapable. Such softness would be desirable from both an aesthetic and comfort viewpoint. It is to such needs that the current invention is directed.

DEFINITIONS

The term "elastic" is used herein to mean any material which, upon application of a biasing force, is stretchable, that is, elongatable, to a stretched, biased length which is at least about 150 percent of its relaxed unbiased length, and which will recover at least 50 percent of its elongation upon release of the stretching, elongating force in less than one minute. A hypothetical example would be a one (1) inch sample of a material which is elongatable to at least 1.50 inches and which, upon being elongated to 1.50 inches and released, will recover to a length of not more than 1.25 inches in less than one minute. Many elastic materials may be stretched by much more than 50 percent of their relaxed length, for example, 80 percent or more, and many of these will recover to substantially their original relaxed length, for example, to within 105 percent of their original relaxed length, upon release of the stretching force.

As used herein, the terms "nonelastic" and "inelastic" shall be interchangeable and refer to any material which does not fall within the definition of "elastic," above.

As used herein, the term "recover" refers to a contraction (or retraction) of a stretched material upon termination of a biasing force following stretching of the material by application of the biasing force. For example, if a material having a relaxed, unbiased length of one (1) inch is elongated 50 percent by stretching to a length of one and one half (1.5) inches, the material would be elongated 50 percent (0.5 inch) and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its one-half (0.5) inch elongation. Recovery may be expressed as [(maximum stretch length−final sample length)/(maximum stretch length−initial sample length)] times 100.

As used herein, the term "nonwoven web" means a web that has a structure of individual fibers or threads which are interlaid, but not in an identifiable, repeating manner. Nonwoven webs have been, in the past, formed by a variety of processes such as, for example, meltblowing processes, spunbonding processes and bonded carded web processes. Laminates containing such web materials may be formed and are considered a nonwoven material laminate.

As used herein, the term "microfibers" means small diameter fibers having an average diameter not greater than about 100 microns, for example, having a diameter of from about 0.5 microns to about 50 microns, more particularly, microfibers may have an average diameter of from about 4 microns to about 40 microns.

As used herein, the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, the disclosure of which is hereby incorporated by reference.

As used herein, the terms "spunbonded fibers" and "spunbond fibers" shall be used interchangeably and shall refer to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbonded nonwoven webs is illustrated in patents such as, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,542,615 to Dobo et al. The disclosures of these patents are hereby incorporated by reference.

As used herein, the term "bonded carded webs" refers to webs that are made from staple fibers which are usually purchased in bales. The bales are placed in a fiberizing unit/picker which separates the fibers. Next, the fibers are sent through a combining or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calender rolls or ultrasonic bonding equipment is used to bond the fibers together, usually in a localized bond pattern through the web and/or alternatively the web may be bonded across its entire surface if so desired. When using bicomponent staple fibers, through-air bonding equipment is, for many applications, especially advantageous.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., and U.S. Pat. No. 5,336,552 to Strack et al. Conjugate fibers are also taught in U.S. Pat. No. 5,382,400 to Pike et al., and may be used to produce crimp in the fibers by using the differential rates of expansion and contraction of the two or more polymers. For two component fibers, the polymers may be present in varying desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein, the term "sheet" means a layer which may be one or more of the following: a scrim, a film, a woven web material, a nonwoven web, a foam, a combination of a nonwoven web and continuous filaments or a combination of any of the foregoing. Desirably, such sheet is selected from a film, a nonwoven web or nonwoven web with continuous filaments.

As used herein, the term "necked material" refers to any material which has been narrowed in at least one dimension by application of a tensioning force in another direction (dimension).

As used herein, the term "neckable material" means any material which can be necked.

As used herein, the term "percent neckdown" refers to the ratio determined by measuring the difference between the un-necked dimension and the necked dimension of the neckable material and then dividing that difference by the un-necked dimension of the neckable material and then multiplying the quotient by 100.

"Neck bonding" refers to the process wherein an elastic member is bonded to a second member (facing) while only the second member (facing) is extended so as to reduce its dimension in the direction orthogonal to the extension. Such materials generally have cross-machine direction stretch.

As used herein, the terms "elastic necked-bonded material" or "neck-bonded laminate" shall be used interchangeably and refer to a laminate material having an elastic sheet joined to a necked material at least at two places. The elastic sheet may be joined to the necked material at intermittent points or may be completely bonded thereto. The joining is accomplished while the elastic sheet and the necked material are in juxtaposed configuration. The elastic necked-bonded material is elastic in a direction generally parallel to the direction of neckdown of the necked material and may be stretched in that direction to the breaking point of the necked material. An elastic necked-bonded material may include more than two layers. For example, the elastic sheet may have necked material joined to both of its sides so that a three-layer composite or laminate of elastic necked-bonded material is formed having a structure of necked material/elastic sheet/necked material. Additional elastic sheets and/or necked material layers may be added. Yet other combinations of elastic sheets and necked materials may be used.

"Stretch bonding" refers to a process wherein an elastic member is bonded to another member while only the elastic member is extended, such as by at least about 25 percent of its relaxed length. "Stretch bonded laminate" refers to a composite elastic material made according to a stretch bonding process, i.e., the layers are joined together when only the elastic layer is in an extended condition so that upon relaxing the layers, the other layer is gathered. Such laminates usually have machine directional stretch properties and may be subsequently stretched to the extent that the other layer gathered between the bond locations allows the elastic material to elongate. The other layer may be made from a variety of materials, such as non-elastic materials or elongatable materials.

The term "elongatable", shall describe the ability of a material to extend without rupture in one direction (such as by about 10 percent from a starting length), but not necessarily including the ability to recover once extended.

"Neck-stretch bonding" generally refers to a process wherein an elastic member is bonded to another member while the elastic member is extended, such as by at least about 25 percent of its relaxed length and the other layer is a necked, non-elastic elongatable layer. "Neck-stretch bonded laminate" refers to a composite elastic material made according to the neck-stretch bonding process, i.e., the layers are joined together when both layers are in an extended condition and then allowed to relax. Such laminates usually have multi or omni-directional stretch properties. Neck stretch bonded laminates are described in U.S. Pat. Nos. 5,116,662 and 5,114,781 each incorporated by reference hereto in its entirety.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible stereospecific geometrical configurations of the molecule. These configurations include, but are not limited to, isotactic, syndiotactic and random symmetries.

As used herein, the terms "machine direction" or MD means the direction along the length of a fabric (such as a woven or nonwoven material) or film in the direction in which it is produced. The terms "cross machine direction," "cross directional," or CD mean the direction across the width of fabric or film, i.e. a direction generally perpendicular to the MD.

The basis weight of nonwoven fabrics or films is usually expressed in ounces of material per square yard (osy) or grams per square meter (g/m² or gsm) and the fiber diameters useful are usually expressed in microns. (Note that to convert from osy to gsm, multiply osy by 33.91). Film thicknesses may also be expressed in microns or mils. 1 mil shall be defined to equal 0.001 inch.

As used herein the term "set" refers to retained elongation in a material sample following the elongation and recovery, i.e. after the material has been stretched and allowed to relax for at least 10 seconds.

As used herein the term "percent set" is the measure of the amount of the material permanently elongated from its original length after being cycled. The remaining strain after the removal of the applied stress is measured as the percent set. The percent set can be described as that location on a graph where the retraction curve of a cycle crosses the elongation axis, and as further discussed below, and is represented by the following formula:

$$\frac{\text{Final length} - \text{Initial length}}{\text{Stretched length} - \text{Initial length}} \times 100$$

The "hysteresis" is determined by first elongating a sample to a given elongation (such as for instance at the 30, 50 percent and 100 percent elongation as noted) and determining the energy required to elongate the sample to the given elongation, and immediately allowing the sample to retract back to its original length and determining the energy recovered during retraction. The hysteresis value determining numbers would then be read for instance at the 30, 50 percent and 100 percent elongation, in either the machine or the cross-machine directions.

$$\text{Hysteresis} = \frac{\text{Energy Extension} - \text{Energy Retraction}}{\text{Energy Extension}} \times 100$$

The percent energy recovered is equal to 100—the value of hysteresis.

As used herein, the term "just formed" shall refer to a laminate or other material that is formed on an in-line process. Essentially, each component of a laminate, such as an elastic layer and a non-elastic layer, are formed in-line with each other immediately prior to their lamination. Such laminate continues to be processed in-line, such as by being printed or otherwise processed.

As used herein, the term "pre-formed" shall refer to a laminate produced from materials made via geographically/physically separated processes, that is processes which are not in-line. Such a pre-formed process may be for example, by providing the laminate material from a storage roll for further processing in another location from where the rolled laminate material was produced.

As used herein, a "stretching apparatus" shall refer to at least one pair of intermeshing grooved rolls, intermeshing discs on parallel axles (also referred to disc on axle arrangements), belt arrangements or tenter frames, which allow for the stretching of a material in either the cross-machine direction or machine direction. In operation, the grooved rolls or discs intermesh to provide material stretch at multiple points across a single direction of a material. Alternatively, such stretching apparatus may include a series of sets of intermeshing grooved rolls or intermeshing discs on axles, or a main grooved roll and a series of satellite grooved rolls positioned about the main grooved roll. Examples of such stretching apparatus may be found in U.S. Pat. No. 4,153,751 to Schwarz, Application WO2004/020174 for Device and Process for Treating Flexible Web By Stretching Between Intermeshing Forming Surfaces to Robert Gerndt et al., filed Aug. 22, 2003, and U.S. application Ser. No. 10/881,064 to Michael T. Morman, for Efficient Necked Bonded Laminates and Methods of Making Same, filed Jun. 30, 2004, each incorporated by reference in its entirety.

As used herein and in the claims, the term "comprising" is inclusive or open-ended and does not exclude additional unrecited elements, compositional components, or method steps. Accordingly, such terms are intended to be synonymous with the words "has", "have", "having", "includes", "including", and any derivatives of these words.

For the purposes of this application, the "draw" shall mean the unit dimension (such as length) of a material after processing divided by the unit dimension (such as length) of that material before processing. For example a length of a material following processing to 4 ft from a starting length of 1 ft would have a draw of 4.

Test Methods

Softness/Cup Crush Test:

The softness of a nonwoven fabric may be measured according to the "cup crush" test. The cup crush test evaluates fabric stiffness by measuring the peak load (also called the "cup crush load" or just "cup crush") and the energy required to crush a specimen and in turn quantify softness of the specimen. The specimen is placed inside a forming cup. The forming cup and the specimen are then placed on a load plate which is mounted on a tensile tester. A foot descends through the open end of the forming cup and "crushes" and distorts the cup-shaped specimen inside. Peak load measured in grams-force (gf) and Energy, measured in gramsforce-length (gf-mm) are the results. The results are a manifestation of the stiffness of the material. The stiffer the material, the higher the peak load and energy values. The softer the material, the lower the values.

The constant rate of extension tensile tester is equipped with a computerized data-acquisition system (such as MTS TestWorks for Windows version 4, from MTS Systems Corporation, Eden Prairie, Minn. 55344-2290) that is capable of calculating peak load and energy, preferably at a minimum data capture rate of 20 data points per second, between two pre-determined distances (15-60 millimeters) in a compression mode. A suitable device for measuring cup crush is a model FTD-G-500 load cell (500 gram range) available from the Schaevitz Company, Pennsauken, N.J. Tensile Testers and load cells can be obtained from Instron Corporation, Canton, Mass. 02021 or Sintech, Inc., P.O. Box 14226, Research Triangle Park, N.C. 27709-4226.

The energy measured is that required for a 4.5 cm diameter hemispherically shaped foot to crush a 23 cm by 23 cm piece of fabric shaped into an approximately 6.5 cm diameter by 6.5 cm tall inverted cup while the cup shaped fabric is surrounded by an approximately 6.5 cm diameter cylinder (forming cup) to maintain a uniform deformation of the cup shaped fabric during testing. An average of 3-5 readings was used. The test is conducted in a standard laboratory atmosphere of 23±2° C. and 50±5% relative humidity. The material should be allowed to reach ambient temperature before testing. The specimen is prepared by placing a retaining ring over a forming stand. The material is then placed over the forming stand. A forming cup is placed over the specimen and the forming stand to conform the specimen into the cup shape. The retaining ring engages the forming cup to secure the specimen in the forming cup. The forming cup is removed with the now-formed specimen inside. The specimen is secured within the forming cup by the retaining ring. The specimen, forming cup, and retaining ring are inverted and placed in the tensile tester. The foot and the forming cup are aligned in the tensile tester to avoid contact between the cup walls and the foot which could affect the readings. The foot (0.5 inch and either made of lightweight nylon or metal) passes through an opening in the bottom of the inverted forming cup to crush the cup-shaped sample inside. The peak load is measured while the foot is descending at a rate of about 406 mm per minute and is measured in grams. The cup crush test also yields a value for the total energy required to crush a sample (the "cup crush energy") which is the energy from the start of the test to the peak load point, i.e. the area under the curve formed by the load in grams on one axis and the distance the foot travels in millimeters on the other. Cup crush energy is therefore reported in gf-mm. Lower cup crush values indicate a softer laminate.

To determine the percent change in cup crush or cup crush energy brought about by processing a material, the same instrument and conditions are used to test a material and post treated sample. The percent change is the ((initial value–final value)/initial value) times 100.

Drape/Drape Stiffness Test:

The drape stiffness test, also sometimes called the cantilever bending test, determines the bending length of a fabric using the principle of cantilever bending of the fabric under its own weight. The bending length is a measure of the interaction between fabric weight and fabric stiffness, as shown by the way in which a fabric bends under its own weight. This is a reflection of the stiffness of the fabric when bent in one plane under the force of gravity. A 1 inch (2.54 cm) by 8 inch (20.3 cm) fabric strip is slid, at 4.75 inches per minute (12 cm/min) in a direction parallel to its long dimension so that its leading edge projects from the edge of a horizontal surface. The longer dimension is the dimension being tested. The length of the overhang is measured when the tip of the specimen is depressed under its own weight to the point where the line joining the tip to the edge of the platform makes a 41.5 degree angle with the horizontal. The longer the overhang (higher numbers) the slower the specimen was to bend, indicating a stiffer fabric.

The drape stiffness is calculated as 0.5×bending length (in inches). A total of 3-5 samples of each fabric were taken. This procedure conforms to ASTM standard test D-1388 except for the fabric length which is different (longer). The test equipment used is a Cantilever Bending tester model 79-10 available from Testing Machines Inc., 400 Bayview Ave., Amityville, N.Y. 11701. The sample should be conditioned to ASTM conditions of 65±2 percent relative humidity and 72±2° F. (22±1° C.), or TAPPI conditions of 50±2 percent relative humidity and 72±1.8° F. prior to testing.

To determine the percent change in drape brought about by processing a material, the same instrument and conditions are used to test a material and post treated sample.

Percent change in drape is ((initial drape–final drape)/initial drape) times 100.

Tensile Strength and Elongation for Necked Bonded Laminate material; The First/Last Cycle Elasticity and Elongation Test:

This tensile test procedure is used to determine the stress/strain curve under cyclic conditions and performing an elongation (at a constant load) test of thermoplastic fabrics such as neck bonded laminates. The test specimen is 3 by 6 inches (with the former being MD and the latter being CD), with each end of the 3 inch direction being placed in the clamps. Using a constant rate of extension tensile testing machine, a cyclic force is applied to the specimen. Set values are obtained over the course of the cyclic testing. This method addresses the testing for the amount of elongation reached when the force applied reaches 2000 g. As the last function in the method, using the same specimen, a strip tensile procedure is performed and the peak load is recorded.

To start, each specimen is started with a preload of 20 g +/−10 g as it is mounted and clamped for testing. The size of the jaw faces are as follows: Both jaws shall have 2 jaw faces measuring 1 inch perpendicular to the direction of the application of the force, and not less than 3 inches parallel to the direction of the application of the force. Each jaw should have a smooth, rubberized, gripping surface. A constant Rate of Extension Tester such as those available from Sintech Corp (models available with TESTWORKS software, such as Sintech 2) from the Sintech Corp. of Cary, N.C., or Instron models from the Instron Corporation of Canton, Mass. are acceptable.

After each sample is cut in the 3 by 6 inch dimensions, insure that the following conditions are followed. Set the distance between the jaws (gage length) at 2.0+/−.05 inch (as measured between top and bottom jaw faces). Set the testing machine speed at 20+/−0.5 inch/min (500+/−10 mm/min). The stop load should be at 2000 g, set elongation measuring point to 30%, first extension at 2000 g, retraction measuring point at 30%, specify % set load at 25 g, and cycle number to 2 unless otherwise noted. The sample should be extended to 100 percent elongation, i.e. to 4 inch gage length total and brought back to 2 inch gage length 2 times, and then sample is elongated to break. The testing should be done in laboratory atmosphere of about 73.5+/−3.6 degree F. and 50+/−5 RH. Mount the specimen securely in the jaws of the testing equipment, with the specimen centrally held in the jaws, prior to testing. The sample is then pulled to a stop load of 2000 g with a crosshead speed of about 500 mm per minute. The measurements taken are the load at elongation, hysteresis loss and load at return. This is used to develop a graphical representation of the results, with load on the y axis and elongation on the x axis. This graph yields a curve with an area thereunder called the Total Energy Absorbed or "TEA". The ratio of the TEA curves for a sample for various cycles is a value independent of material, basis weight and sample width that can be compared to other samples.

For the samples, the term "control" designates that neck bonded laminate without grooved roll treatment, while the term "test specimen" designates the neck bonded laminate with grooved roll treatment as described below.

SUMMARY OF THE INVENTION

A method for producing a single direction elastic laminate includes the steps of providing a one direction elastic laminate material including at least one elastic layer and one facing layer and having a single or original direction of elasticity and coursing the one direction elastic laminate material through at least one stretching apparatus, such that the stretching apparatus stretches the laminate material in a direction perpendicular to the single/original direction of elasticity of the elastic laminate material, thereby producing a material that is extended in a direction perpendicular to the direction of elasticity and also demonstrates enhanced elastic performance (efficiency) in the single (original) direction of elasticity by at least reducing the percent set, when compared to similar materials that have not been stretched.

In an alternative embodiment of the inventive method, the one direction elastic laminate material is either a necked bonded laminate or a stretch bonded laminate. In still a further alternative embodiment of the inventive method, the stretching apparatus is selected from the group consisting of intermeshing grooved rolls, intermeshing discs on axles, belts and tenter frames. In yet a further alternative embodiment of the inventive method, the step of stretching the elastic laminate material is through two sets of stretching apparatus, such that the laminate material is stretched both in a direction perpendicular to the single direction of elasticity and also in a direction parallel to the single direction of elasticity. In yet a further alternative embodiment of the inventive method, the laminate is a pre-formed material. The invention also contemplates materials made by the inventive method.

A method for producing a cross-machine direction elastic laminate includes the steps of providing a neck bonded laminate material including at least one elastic layer and one facing layer and having a cross-machine direction of elasticity, and coursing the neck bonded laminate material through at least one stretching apparatus, such that the stretching apparatus stretches the laminate material in the machine direction, thereby producing a material that is extended in the machine direction and also demonstrates enhanced elastic performance efficiency in the cross-machine direction, when compared to similar laminate material that has not be so stretched. In an alternative embodiment of the method, the stretching apparatus is at least one set of intermeshing grooved rolls. In still a further alternative embodiment of the method, the neck bonded laminate material is coursed between two stretching apparatus. In still a further alternative embodiment of the method, each of two stretching apparatus stretch the laminate in perpendicular or non-parallel directions. In yet another alternative embodiment of the inventive method, the elastic layer is either a film, a nonwoven web sheet, a foam sheet, elastic scrim or a combination thereof. In yet another alternative of the inventive method, the laminate is a pre-formed material. The invention also encompasses material made by the method.

A method for producing a machine direction elastic laminate includes the steps of providing a stretch bonded laminate material including at least one elastic layer and one facing layer and having a machine direction elasticity and coursing the stretch bonded laminate material through at least one stretching apparatus, such that the stretching apparatus stretches the laminate material in the cross machine direction, thereby producing a material that is extended in the cross-machine direction and also demonstrates enhanced elastic performance in the machine direction by reduced percent set, when compared to similar materials that have not been stretched. In an alternative embodiment of the inventive method, the elastic layer is selected from the group consisting of a nonwoven web, a film, an array of parallel filaments, a foam sheet, elastic scrim and a combination thereof. In still another alternative embodiment of the inventive method, the stretching apparatus is selected from the group consisting of intermeshing grooved rolls, intermeshing discs on axles, tenter frames, and belt arrangements. In still another alternative embodiment of the inventive method, the laminate is coursed through two stretching apparatus. In still another alternative embodiment of the inventive method, the laminate is coursed through two stretching apparatus and each of the stretching apparatus stretch the laminate in non-parallel directions (such as for example, perpendicular directions). In yet another alternative embodiment of the inventive method, the laminate is of a pre-formed material. The invention also encompasses a material produced by the method. In still yet another alternative embodiment, the invention encompasses personal care articles made from materials produced from any of the above method embodiments, such as for example adult incontinence products.

In still a further alternative embodiment of the invention, a method for producing an elastic laminate includes the steps of providing an elastic laminate material including at least one elastic layer and one facing layer and having an original direction of elasticity; coursing the elastic laminate material through at least one stretching apparatus, such that the stretching apparatus stretches the laminate material in a direction perpendicular to the original direction of elasticity of the elastic laminate material, thereby producing a material that is extended in a direction generally perpendicular to the original direction of elasticity, such that elasticity is imparted to the material in the direction generally perpendicular to the original direction of elasticity. In yet another alternative embodiment of the inventive method, the produced material demonstrates enhanced elastic performance in the original direction of elasticity. In still a further alternative embodiment of the inventive method, the elastic laminate is a stretch bonded laminate comprising an elastic layer of one or more film materials, web materials, scrim or foam materials or a combination of such. In still a further alternative embodiment of the inventive method, the material is used in a personal care product, such as for example, an adult incontinence product. In still a further alternative embodiment of the inventive method, the produced material demonstrates a cup crush load value of between about 100 to 150 gf. In still a further alternative embodiment of the inventive method, the produced material demonstrates a cup crush load value of between about 20 and 80 percent, alternatively between about 30 and 70 percent, and still further between about 40 and 65 percent of a similar laminate material that has not gone through the production method. In still a further alternative embodiment of the inventive method, the produced material demonstrates a normalized cup crush load value of between about 1-2 gf/gsm. In still a further alternative embodiment of the inventive method, the produced material demonstrates a cup crush energy of between about 1700 and 2500 gf-mm. In still a further alternative embodiment of the inventive method, the produced material demonstrates a normalized cup crush energy of between about 20 and 30 gf-mm. In yet a further alternative embodiment of the inventive method, the produced material demonstrates a cup crush energy of between about 10 and 75 percent, alternatively between about 20 and 65 percent and still alternatively between about 30 and 55 percent of a similar material that has not been produced by the inventive method.

In yet still a further alternative embodiment of the inventive method, the material produced (with original cross-machine direction elasticity) demonstrates a machine-direction drape value of between about 2 and 3 cm. In still a further alternative embodiment of the inventive method, the material produced demonstrates a drape value in the direction perpendicular to the original direction of elasticity, of between about 20 and 80 percent, alternatively between about 30 and 70 percent, and still alternatively between about 40 and 65 percent of a similar material that has not been produced in accordance with the inventive method.

BRIEF DESCRIPTION OF THE DRAWINGS

FIG. 1 is a schematic representation of an exemplary process for producing an elastic laminate in accordance with the invention.

FIG. 2A is a cross-sectional representation of an intermeshing grooved roll arrangement for producing an elastic laminate in accordance with the invention.

DETAILED DESCRIPTION OF THE INVENTION

Figure 2B:
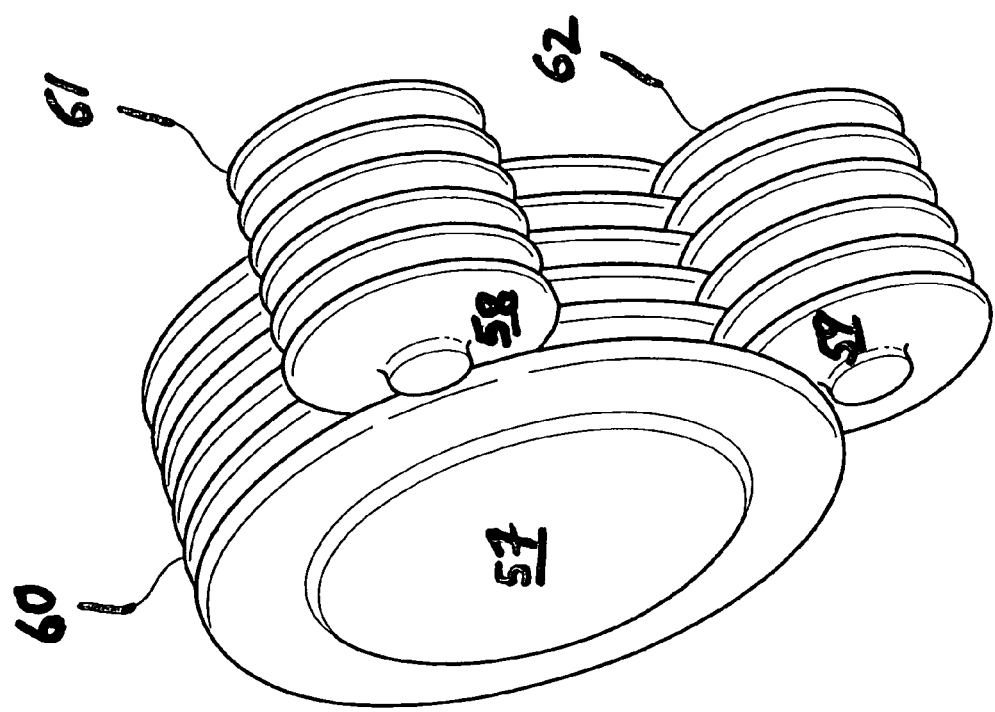
FIG. 2B is a perspective view of a satellite grooved roll arrangement for producing an elastic laminate (by stretching the laminate in the cross-machine direction) in accordance with the invention.

In a method involving reduced production steps, a preformed laminate material which already demonstrates elasticity in one direction, that has stretch and recovery properties in at least one direction, is coursed through an intermeshing grooved roll arrangement, intermeshing disc on axle apparatus/arrangement, or through another stretching apparatus (such as tenter frames or belt stretchers) to provide extension/stretch attributes in at least a direction perpendicular to the direction of stretch and recovery of the pre-formed laminate material. For example, in such process a pre-formed necked bonded laminate which demonstrates cross-machine direction stretch and recovery attributes, is coursed through a grooved roll arrangement with grooves running across the cross-machine direction, such that the material is stretched/extended in the machine direction. Similarly, a pre-formed stretch bonded laminate with stretch and recovery attributes in the machine direction, is coursed through a groove roll arrangement or intermeshing disc arrangement with grooves or discs running in the machine direction, so as to provide stretch/extension in the cross-machine direction. For the purposes of this application, the term "machine direction grooved roll" shall refer to a grooved roll that stretches material in the cross-machine direction, and the term "cross-machine direction grooved roll" shall refer to a grooved roll that stretches material in the machine direction. Alternatively, tenter frames or belt stretching apparatus may be used to stretch the laminate in the cross-machine direction. It has been found that this one-way, one step laminate treatment allows for extension of the material in a new direction, in addition to the high extension originally provided for in the pre-formed neck bonded laminate or stretch bonded laminate. Such extension in the direction perpendicular to the direction of elasticity provides increased softness to the material and also enhances the elastic efficiency of the elastic material by reducing the percent set of the material (on the first stretch in use). The first stretch in use will be the consumer's first stretch of a product which incorporates the material. Further in the case of stretch bonded laminates produced by the method, in which the elastic layer of the laminate is a continuous elastic sheet, such as a film, web or foam (as opposed to only a series of parallel elastic continuous filaments), the produced laminate may also demonstrate elasticity in both the machine and cross-machine directions.

Further, using an intermeshing grooved roll arrangement or an intermeshing disc arrangement that is oriented such that it stretches an elastic laminate in the same direction as the pre-formed laminate's direction of stretch will produce in the case of a neck bonded laminate a very high (additive) cross-direction stretch, or a stretch bonded laminate with very high (additive) machine-direction stretch, when compared to similar laminates that have not been stretched. Essentially, the additional stretching in the direction of original stretch, further permanently lengthens the spunbond, thereby providing additional stretch potential to the material. Therefore, using multiple sets of non-parallel oriented stretching apparatus (such as for example, perpendicularly oriented) on a single direction elastic laminate, will both extend the laminate material in a direction perpendicular to the direction of material elasticity (thereby leading to a softer material) and also enhance the material's elasticity both by reducing percent set and providing added stretch capability, when compared to similar laminate materials that have not been stretched in accordance with the inventive method. For example, using multiple sets of non-parallel oriented grooved rolls (grooves of one set perpendicular to the grooves of another set, or at some other angle with respect to each other) to stretch a neck bonded laminate will both extend the laminate in the direction without elasticity, and also increase the level of elasticity in the cross-machine direction. Similarly, using such rolls on a stretch bonded laminate will extend the laminate in the cross-machine direction and also provide enhanced elasticity in the machine direction. As previously stated, depending on the type of stretch bonded laminate utilized (such as an elastic layer based on a continuous sheet as opposed to just elastic filaments in the machine direction), such process may also provide elasticity to the laminate in the direction perpendicular to the original direction (MD) of stretch. Additionally, using multiple sets of grooved rolls or discs (having one set of machine direction grooves or discs and a second set of cross machine direction grooves) on a neck stretch bonded laminate will increase both machine and cross-machine direction stretch/elasticity, especially if the elastic sheet layer has a cross machine and machine direction component (such as a web, scrim, film, or foam).

Therefore in a first embodiment of the inventive method, a method for producing a machine direction or cross-machine direction elastic laminate includes the steps of providing a one direction elastic laminate material including at least one elastic layer and one facing layer and having a single direction of elasticity, and coursing the one direction elastic laminate material through at least one stretching apparatus, such that the stretching apparatus stretches the laminate material in a direction perpendicular to the single direction of elasticity, thereby producing a material that is extended in a direction perpendicular to the direction of elasticity and also demonstrates enhanced elastic performance efficiency in the single direction of elasticity (by reducing percent set experienced in first use). If the elastic layer retracts the material to about its original dimension in the direction that the material was stretched during processing, the material will have elasticity in that direction.

As can be see in FIG. 1, such a method is schematically illustrated at 10. A pre-formed laminate material, such as either a neck bonded laminate, a stretch bonded laminate, or a neck stretch bonded laminate is unwound from unwind roll 20 such that the laminate 30 is fed to stretching apparatus 40. While this method can be used with an in-line production method, it is particularly desirable for use with a pre-formed material production arrangement. In the illustrated embodiment, the stretching apparatus is shown as a set of intermeshing grooved rolls 45 and 46. Following stretching (in either the machine direction or cross-machine direction, depending on the direction of elasticity of the starting laminate) the laminate 47 is fed to a winder roll 48, or other processing station (not shown). For example, such laminate may be apertured or otherwise processed to impart additional functionality to the material. In another example, such laminate may be printed with an elastomeric composition to obtain multi-directional stretch properties.

The stretching apparatus is selected from the group consisting of intermeshing machine direction or cross-machine direction grooved rolls, intermeshing discs on axles, belts and tenter frames. For example, a cross-sectional view of intermeshing grooved rolls is shown in FIG. 2A. As seen in FIG. 2A, the grooved rolls are defined by fins and channels along their surfaces. FIG. 2A is an enlarged partial cross sectional view of an engaged nip of intermeshing grooved rolls. While, for purposes of more clearly illustrating the nip, the path of web 49 is only shown partially across the nip (coming towards the viewer), it will be apparent that the web may and will normally extend completely across the nip. As shown, the grooves 50 of roll 51 intermesh or accommodate the fins 52 between the grooves 53 of roll 54. The intermeshing, in this case, maintains spacing, W, between the respective groove walls 55, 56 that is wider than the thickness of web 49 with the result that the web is stretched without being compressed. As shown, H measures the fin height, and E measures the depth of engagement. The number of grooves per inch is measured by counting the number of fins, tip to tip (peak to peak), per inch along the roll.

The number of grooves may be varied widely to achieve desired results. For example, for stretching of lightweight laminates of film and nonwoven for disposable personal care product applications such as a backing/outercover component, the number of grooves useful may vary from about 3 to about 15 per inch, although greater or fewer are contemplated. For instance, in one particular embodiment, the number of grooves is between about 5 and 12 grooves per inch. In a further alternative embodiment, the number of grooves is between 5 and 10 per inch. Essentially, in one particular embodiment, the peak to peak distance of the fins may be varied from about 0.333 inch to about 0.0666 inch. In an alternative embodiment the peak to peak distance may be between about 0.200 inch to about 0.083 inch. The engagement of the fins and grooves of the grooved rolls may be from about 0 to 0.300 inch. In an alternative embodiment, the engagement of fins in grooves is between about 0.010 inch to about 0.200 inch. In another embodiment, the engagement may be between about 0.070 inch to about 0.150 inch. Desirably, in one embodiment the total stretch of the material in the CD direction is between about 2.0-2.75× and an engagement of between about 0.100 inch to about 0.150 inch (at about 8 grooves per inch). In some applications, the grooves or discs may be of a macroscopic level, as described in U.S. application Ser. No. 10/881,064 to Michael T. Morman, for Efficient Necked Bonded Laminates and Methods of Making Same, filed Jun. 30, 2004, incorporated by reference in its entirety. In such an embodiment, the amount of fins or discs is less across any given area, as the fins or discs are spaced further apart. Additionally, for some applications, it may be important that the compression of the material be avoided, and the shape of the intermeshing grooves may be selected for that purpose. Furthermore, the depth of engagement as the grooves intermesh may also be varied so as to achieve the desired stretch level. It is a feature of the present invention that high stretch levels may be attained in localized areas in steps of engagement that avoid single, harsh impact that might damage fragile materials.

The rolls of such arrangements or discs may be constructed of steel or other materials satisfactory for the intended use conditions as will be apparent to those skilled in the art. Also, it is not necessary that the same material be used for all the rolls or discs. For example, a set of grooved rolls may be manufactured from two different metallic or rubber materials. In another embodiment, a satellite and central anvil roll arrangement may be utilized and can incorporate multiple materials. Such an arrangement is illustrated in FIG. 2B. In such an arrangement, the anvil roll may for example, be constructed of hard rubber or other more resilient material so as to impact a flexible web under less stressful conditions. The temperature of one or more of the rolls may be controlled by heating or cooling to also change the stretching conditions.

To a significant extent, the material being treated will determine the desired configuration of the equipment. For example, treatment of heavy weight materials may dictate that the spacing of the grooves or discs be increased over those parameters for lighter weight materials. More elastic materials may also suggest that the spacing may be increased without damage to the web, however, the less elastic component of a laminate will also be a consideration.

In a satellite roll arrangement, the satellite rolls are positioned in working engagement with the grooved surface of the anvil roll such that they are shaped and positioned to intermesh or fit within the grooves of the anvil roll about the anvil roll. The number of satellite rolls to be employed may be varied, and the satellite rolls are preferably adapted to be moved in and out of engagement so that the number may be readily changed as desired. The rolls are desirably driven at speeds matched to the desired effective engagement by one or more motors (not shown).

As shown in FIG. 2B illustrating a perspective view of a satellite roll arrangement, anvil roll 57 is engaged by satellite rolls 58 and 59 which operate to apply a stretching force to a laminate as the laminate passes through the nips formed between the anvil and satellite rolls. In this case, the fins of one of the satellite rolls extend into mating grooves of the anvil roll to a lesser extent than do the fins of the other satellite roll. In this manner, stretching forces applied to the laminate may be gradually increased so that there is a reduced tendency to tear or otherwise damage the laminate and yet stretch to a high degree. It will be apparent that varying the mating engagement of the rolls in the fins/grooves (60, 61, 62) in this manner may be done with any or all of the satellite rolls and may occur in any order of increasing or decreasing engagement as desired.

Figure 2C:
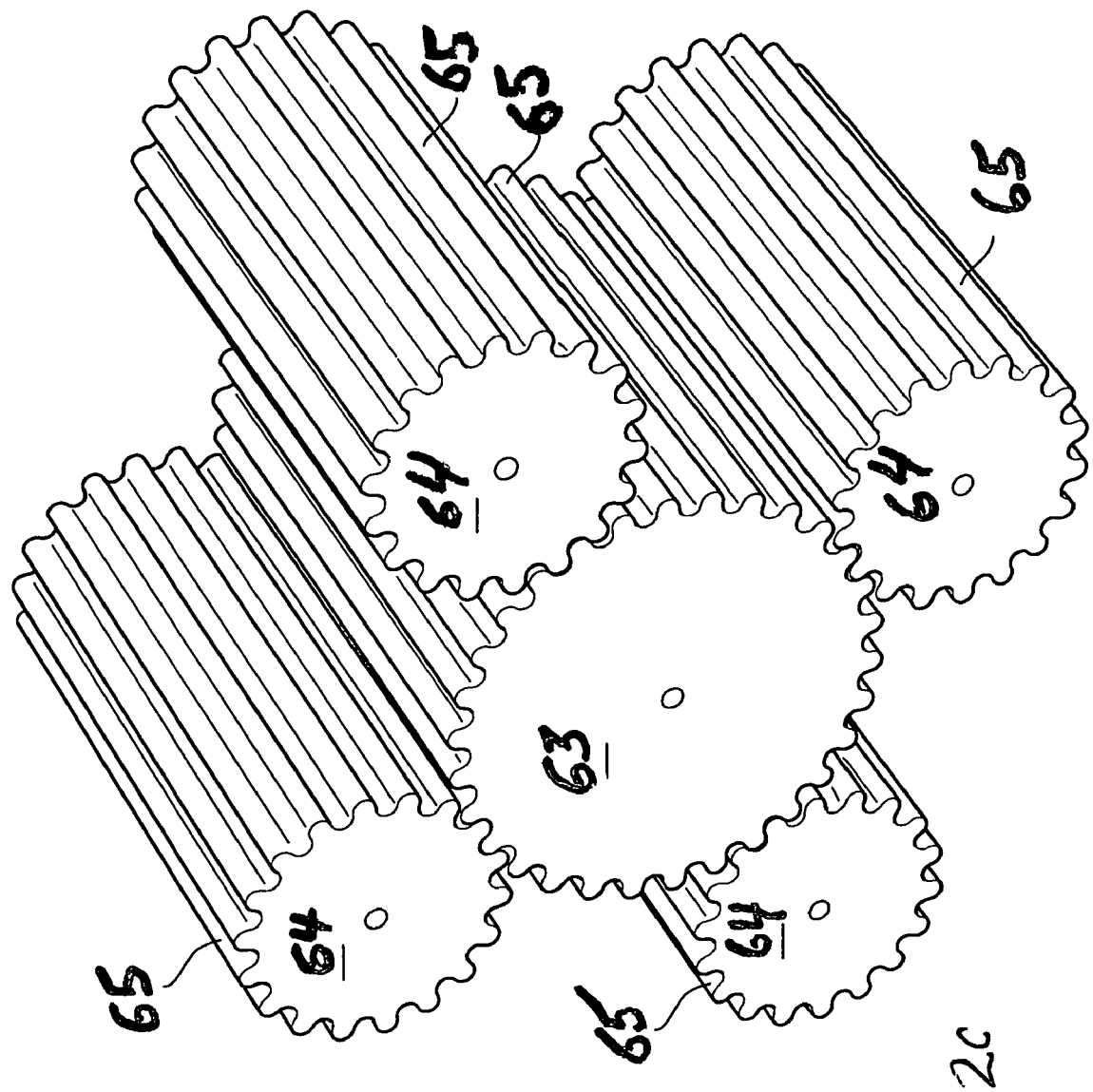
FIG. 2C is a perspective view of a satellite grooved roll arrangement for producing an elastic laminate (by stretching the laminate in the machine direction) in accordance with the invention.

It should be appreciated that while in FIG. 2B, the grooves are positioned such that they stretch the material in the cross-machine direction (for the purposes of stretching stretch bonded laminate materials), the grooves may also run in a direction perpendicular to those shown in FIG. 2B, as can be seen in FIG. 2C. As can be see in FIG. 2C showing a perspective view of a satellite roll arrangement, a central anvil roll 63 is surrounded by satellite rolls 64, with grooves running along the cross-machine direction so as to stretch the material in the machine direction. In this fashion, a neck bonded laminate may be stretched in the machine direction.

Figure 3:
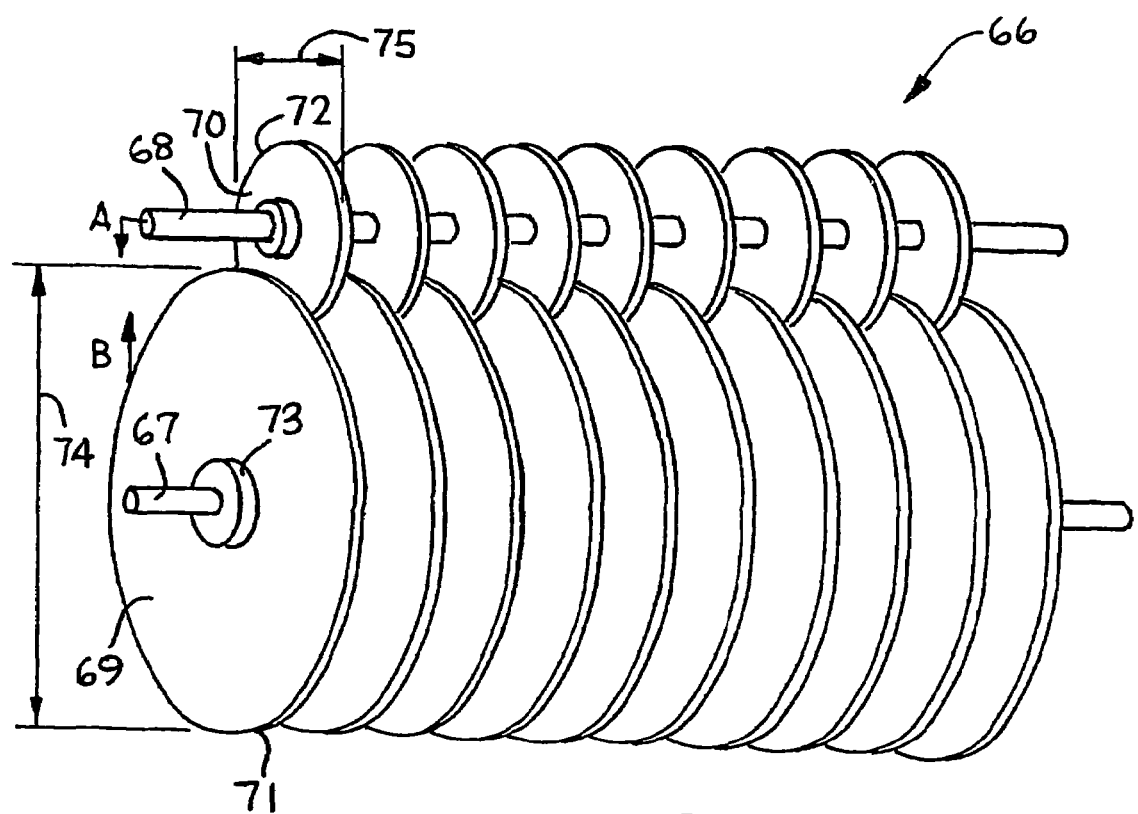
FIG. 3 is a perspective view of discs on axles arrangement (for stretching the laminate in the cross-machine direction) that may be used in accordance with the invention.

As can be seen in FIG. 3, a perspective view of a "disc on axle" apparatus arrangement is illustrated. Such a macroscopic disc arrangement can be used to stretch laminate material between intermeshing/engaged macroscopic discs that are positioned along parallel and adjacent axle shafts. In one embodiment, the discs are at least 1 inch in diameter and may range in size to about 12 inches in diameter or greater. Desirably such discs are manufactured from rigid material (as with the grooved rolls) such as metal, molded resins or rubbers. The disc design and set up minimizes material contact with metal surfaces and especially sharp metal edges that are encountered with microscopic grooved rolls. It is therefore contemplated that the discs will include rounded edges to further minimize contacting the material with harsh sharp edging. It is also contemplated that the individual discs adjustably slide on the axle shafts into position such that spaces between the discs may be readily changeable. However, it is contemplated that "spacers" may be used to maintain separation between the discs, if the discs do not themselves include other known axle locking mechanisms. Such discs may be freely rotatable about the axles or held fast to the axles (in which case the axles would be rotatable) or a combination of both. Such spacers may include ball bearings to provide for free movement of adjacent discs. Similarly, such discs may likewise include ball bearings around their core (hole for receiving the axle shaft) to provide for free independent movement about the axles. In such a fashion, the discs can move at different revolutions per minute to accommodate differing diameters. In a further alternative embodiment, such discs are held in place and the axle is operated to move, rather than the discs freely moving about the axle. Still in a further alternative embodiment, one or more shafts are motor driven while others are not.

Using discs of varying diameters (which is one embodiment contemplated) necessitates using individual free rotating discs as there is the same circumferential surface speed between discs necessitating different revolutions per minute (RPMs). Such a feature cannot be accomplished with grooved rolls.

At least two axle shafts with individual discs can engage (intermesh) such that the edges of such discs overlap (that is pass alongside or between discs on the other axle), during running of material through a nip formed by the discs. Desirably, in one embodiment, such discs are capable of being independently driven and adjusted toward or away from each other, (as shown as A and B in FIG. 3) as with the previously described grooved roll arrangements.

As can be seen in FIG. 3, the disc and axle arrangement 66 includes central shafts 67, 68, about which are positioned discs 69, 70. In one embodiment the discs are of equal diameters along each axle, and between all intermeshing axles (not shown). In a second embodiment, the discs are of the same diameter 74, 75 about one axle, and of different diameters between intermeshing discs (as shown, where one diameter 74 is larger than the other 75). As with the previously described satellite grooved roll arrangement, the disc on axle arrangement may include any number of satellite axles and discs that can engage to different disc depths with progressively more material stretching as material passes around the central largest axle. Alternatively, each of the satellite shafts may include discs at nonoverlapping portions about the central shaft, such that different portions of the material to be stretched would be stretched by different satellite disc and axle components around the central disc and axle shaft. Alternatively, such axle disc arrangement may include only two shafts (as shown).

The disc and axle arrangement are positioned in the process such that the disc outer edges 71 and 72 are aligned with the machine direction. As previously stated with respect to the grooved roll apparatus, one or more of the axles may be capable of movement A, B with respect to each other to provide for varying degrees of intermeshing. Spacers 73 may be used to separate the discs, or the discs may be held in place by other known mechanisms.

In yet a further alternative embodiment of the inventive method, the step of stretching the elastic laminate material is through two sets of stretching apparatus, such that the laminate material is stretched both in a direction perpendicular to the single direction of elasticity and also in a direction parallel to the single direction of elasticity.

A method for producing a cross-machine direction elastic laminate includes the steps of providing a neck-bonded laminate material including at least one elastic layer and one facing layer and having an original cross-machine direction of elasticity, and coursing the neck bonded laminate material through at least one stretching apparatus, as previously described in FIG. 2C, such that the stretching apparatus stretches the laminate material in the machine direction, thereby producing a material that extends in the machine direction and also enhances the elastic performance of the laminate in the cross-machine direction. In an alternative embodiment of the method, the stretching apparatus is at least one set of intermeshing grooved rolls. In still a further alternative embodiment of the method, the neck bonded laminate material is coursed between two stretching apparatus. In still a further alternative embodiment of the method, each of two stretching apparatus stretch the laminate in perpendicular directions. In yet another alternative embodiment of the inventive method, the elastic layer is either a film, a nonwoven sheet, a foam sheet or a combination thereof.

A method for producing a machine direction elastic laminate includes the steps of providing a stretch bonded laminate material including at least one elastic layer and one facing layer and having an original machine direction elasticity and coursing the stretch bonded laminate material through at least one stretching apparatus as previously described in FIGS. 2A and 2B, such that the stretching apparatus stretches the laminate material in the cross machine direction, thereby producing a material that extends in the cross-machine direction and also enhances the elastic performance of the laminate in the machine direction. In an alternative embodiment of the inventive method, the elastic layer is selected from the group consisting of a nonwoven web, a film, an array of parallel continuous filaments, a foam sheet and a combination thereof. Such parallel continuous filaments may be solution spun or extruded. In still another alternative embodiment of the inventive method, the elastic layer is selected from the group consisting of a continuous elastic sheet, such as a web, film or foam sheet. In such an embodiment, the laminate would demonstrate both machine and cross machine direction elasticity following production by the inventive method. In still another alternative embodiment of the inventive method, the stretching apparatus is selected from the group consisting of intermeshing grooved rolls, intermeshing discs on axles, tenter frames, and belt arrangements. In still another alternative embodiment of the inventive method, the laminate is coursed through two stretching apparatus. In still another alternative embodiment of the inventive method, the laminate is coursed through two stretching apparatus and each of the stretching apparatus stretch the laminate in non-parallel directions (such as for example perpendicular directions).

Desirably such elastic layer is either a film, a woven web, a nonwoven web, an array of parallel continuous filaments, a foam sheet material, or a combination thereof made from a polymer with elastic functionality when in sheet form. If the elastic sheet is produced from a nonwoven web, it may for example be made from spunbond, meltblown, or carded web materials. The fibers themselves, may be homocomponent or bicomponent in nature. The elastic layer is desirably produced from elastomers such as styrenic block copolymers available from the Kraton Polymers of Houston, Tex. under the designation KRATON G and D. Other such styrenic block copolymers are available from Septon Company of America, Dexco Polymers, and Dynasol of Spain. Still other exemplary elastomeric materials which may be used to form the elastic sheet include polyurethane elastomeric materials such as, for example, those available under the trademark ESTANE from Noveon of Cleveland, Ohio, polyamide elastomeric materials such as, for example, those available under the designation PEBAX from AtoFina Chemicals Inc. of Philadelphia, Pa., and polyester elastomeric materials such as, for example, those available under the trade designation Hytrel from E. I. DuPont De Nemours & Company. Formation of elastic sheets from polyester elastic materials is disclosed in, for example, U.S. Pat. No. 4,741,949 to Morman et al., hereby incorporated by reference. Additionally, less elastic materials may be used as the elastic component, such as single site catalyzed polyolefins. Such single site catalyzed polyolefins include metallocene-catalyzed polyolefins and constrained geometry polyolefins, available from either ExxonMobil or Dow Chemical Company. Furthermore, a blend of two or more of the aforementioned polymers may be used as the primary component of the elastic layer.

A polyolefin may also be blended with the elastomeric polymer to improve the processability of the composition. The polyolefin must be one which, when so blended and subjected to an appropriate combination of elevated pressure and elevated temperature conditions, is extrudable, in blended form, with the elastomeric polymer. Useful blending polyolefin materials include, for example, polyethylene, polypropylene and polybutene, including ethylene copolymers, propylene copolymers and butene copolymers. Two or more of the polyolefins may be utilized. Extrudable blends of elastomeric polymers and polyolefins are disclosed in, for example, U.S. Pat. No. 4,663,220 to Wisneski et al., hereby incorporated by reference.

The elastic layer may also be a pressure sensitive elastomer adhesive sheet. For example, the elastic material itself may be tacky or, alternatively, a compatible tackifying resin may be added to the extrudable elastomeric compositions described above to provide an elastomeric sheet that can act as a pressure sensitive adhesive, e.g., to bond the elastomeric sheet to a tensioned, necked nonelastic web. In regard to the tackifying resins and tackified extrudable elastomeric compositions, note the resins and compositions as described in U.S. Pat. No. 4,789,699 of J. S. Keiffer and T. J. Wisneski, the disclosure of which is hereby incorporated by reference.

Any tackifier resin can be used which is compatible with the elastomer polymer and can withstand the high processing (e.g., extrusion) temperatures. If blending materials such as, for example, polyolefins or extending oils are used, the tackifier resin should also be compatible with those blending materials. Generally, hydrogenated hydrocarbon resins are preferred tackifying resins, because of their better temperature stability. Other tackifying resins which are compatible with the other components of the composition and can withstand the high processing temperatures, can also be used. A pressure sensitive elastomer adhesive may include, for example, from about 40 to about 80 percent by weight elastomeric polymer, from about 5 to about 40 percent polyolefin and from about 5 to about 40 percent resin tackifier.

Additionally, the elastic layer may be a multilayer material in which one or more of the layers contain a mixture of elastic and nonelastic fibers or particulates. For an example of the latter type of elastic web, reference is made to U.S. Pat. No. 4,209,563, incorporated herein by reference, in which elastomeric and non-elastomeric fibers are commingled to form a single coherent web of randomly dispersed fibers. Another example of such a composite web would be one made by a technique such as disclosed in U.S. Pat. No. 4,100,324 also incorporated herein by reference. That patent discloses a nonwoven material which includes a mixture of meltblown thermoplastic fibers and other materials. The fibers and other materials are combined in the gas stream in which the meltblown fibers are formed so that an intimate entangled commingling of meltblown fibers and other materials, e.g., wood pulp, staple fibers or particulates such as, for example hydrocolloid (hydrogel) particulates commonly referred to as superabsorbents occurs prior to collection of the fibers upon a collecting device to form a coherent web of randomly dispersed fibers. The elastic sheet layer may also be further processed such as by slitting or aperturing stations prior to lamination with a necked facing.

Elastic layers can be used having basis weights less than 0.5 osy (ounces per square yard), for example, from about 0.1 to about 0.4 osy, or alternatively between about 0.25 to about 0.4 osy. Such extremely low basis weight sheets are useful for economic reasons, particularly for use in disposable products. Additionally, elastic sheets having higher basis weights such as, for example, from about 0.5 to about 10 osy may also be used.

The facing layer(s) may be a necked material (if the elastic laminate is a neck bonded laminate or a neck stretch bonded laminate) or an unnecked material (if the elastic laminate is a stretch bonded laminate). The facing layer(s) may be in either instance, a nonwoven material such as for example, a spunbonded web, a meltblown web or bonded carded web, or alternatively a woven or knit material. If the necked material is a web of meltblown fibers, it may include meltblown microfibers. The facing layer(s) may be made of fiber forming polymers such as, for example, polyolefins, polyesters, as well as nylons. Exemplary polyolefins include one or more of polypropylene, polyethylene, ethylene copolymers, propylene copolymers, butene copolymers and blends of such polymers.

In one embodiment of the present invention, the facing layer is a necked nonwoven layer and is a multilayer material having, for example, at least one layer of spunbonded web joined to at least one layer of meltblown web, bonded carded web or other suitable material. For example, the facing may be a multilayer spunbond/meltblown/spunbond material having a first layer of spunbonded polypropylene having a basis weight from about 0.2 to about 8 ounces per square yard (osy), a layer of meltblown polypropylene having a basis weight from about 0.2 to about 4 osy, and a second layer of spunbonded polypropylene having a basis weight of about 0.2 to about 8 osy. Alternatively, the facing layer material may be a single layer of material such as, for example, a necked spunbonded web having a basis weight of from about 0.2 to about 10 osy or a meltblown web having a basis weight of from about 0.2 to about 8 osy that is applied to both sides of an elastic layer.

The facing layer material may also be a composite material made of a mixture of two or more different fibers of different composition or a mixture of fibers and particulates. Such mixtures may be formed by adding fibers and/or particulates to the gas stream in which meltblown fibers are carried so that an intimate entangled commingling of meltblown fibers and other materials occurs as previously described. The facing layer material may also include bicomponent fibers or conjugate fibers as well.

If the facing layer is a nonwoven web of fibers, the fibers should be joined by interfiber bonding to form a coherent web structure which is able to withstand necking if it is to be necked. Interfiber bonding may be produced by entanglement between individual fibers. The fiber entangling is inherent in the meltblown process but may be generated or increased by processes such as, for example, hydraulic entangling or needlepunching. Alternatively and/or additionally a bonding agent may be used to increase the desired bonding. Alternatively, if the facing layer is a spunbond web, it can be held together by thermal bonding such as by the use of a Ramisch (patterned roll).

The facing layer(s) and the elastic layer may be completely bonded together and still provide a composite elastic material with good stretch properties. That is, a composite elastic material may be formed by joining either a necked facing layer to an elastic layer or a stretched elastic layer to a facing layer utilizing bonding surfaces such as, for example, smooth rollers or platens to provide a high bond surface area. A composite elastic laminate may also be formed utilizing a bonding pattern. Necked or unnecked materials may be joined to the elastic layer at least at two places by any suitable means such as, for example, thermal bonding or ultrasonic welding which softens at least portions of at least one of the materials, usually the elastic layer because the elastomeric materials used for forming the elastic layer have a lower softening point than the components of the facing layer. Joining may be produced by applying heat and/or pressure to the overlaid elastic layer and the necked facing layer by heating these portions (or the overlaid layer) to at least the softening temperature of the material with the lowest softening temperature to form a reasonably strong and permanent bond between the re-solidified softened portions of the elastic layer and the facing layer. Additionally, such bonding arrangement may utilize an adhesive as long as the adhesive does not significantly impact the elastic performance of the laminate. Additionally, such bonding arrangement may utilize an entangling process. The laminate may also be bonded using ultrasonic bonding technology.

With regard to thermal bonding, one skilled in the art will appreciate that the temperature to which the materials, or at least the bond sites thereof, are heated for heat-bonding will depend not only on the temperature of the heated roll(s) or other heat sources but on the residence time of the materials on the heated surfaces, the basis weights of the materials and their specific heats and thermal conductivities. However, for a given combination of materials, and in view of the herein contained disclosure, the processing conditions necessary to achieve satisfactory bonding can be readily determined by one of skill in the art. It should also be recognized that in the case of neck and stretch bonded laminates, facing layers can be applied to one or more sides of an elastic layer. For example, a neck bonded laminate may be a sandwich of an elastic layer between two necked facing layers.

Figure 4:
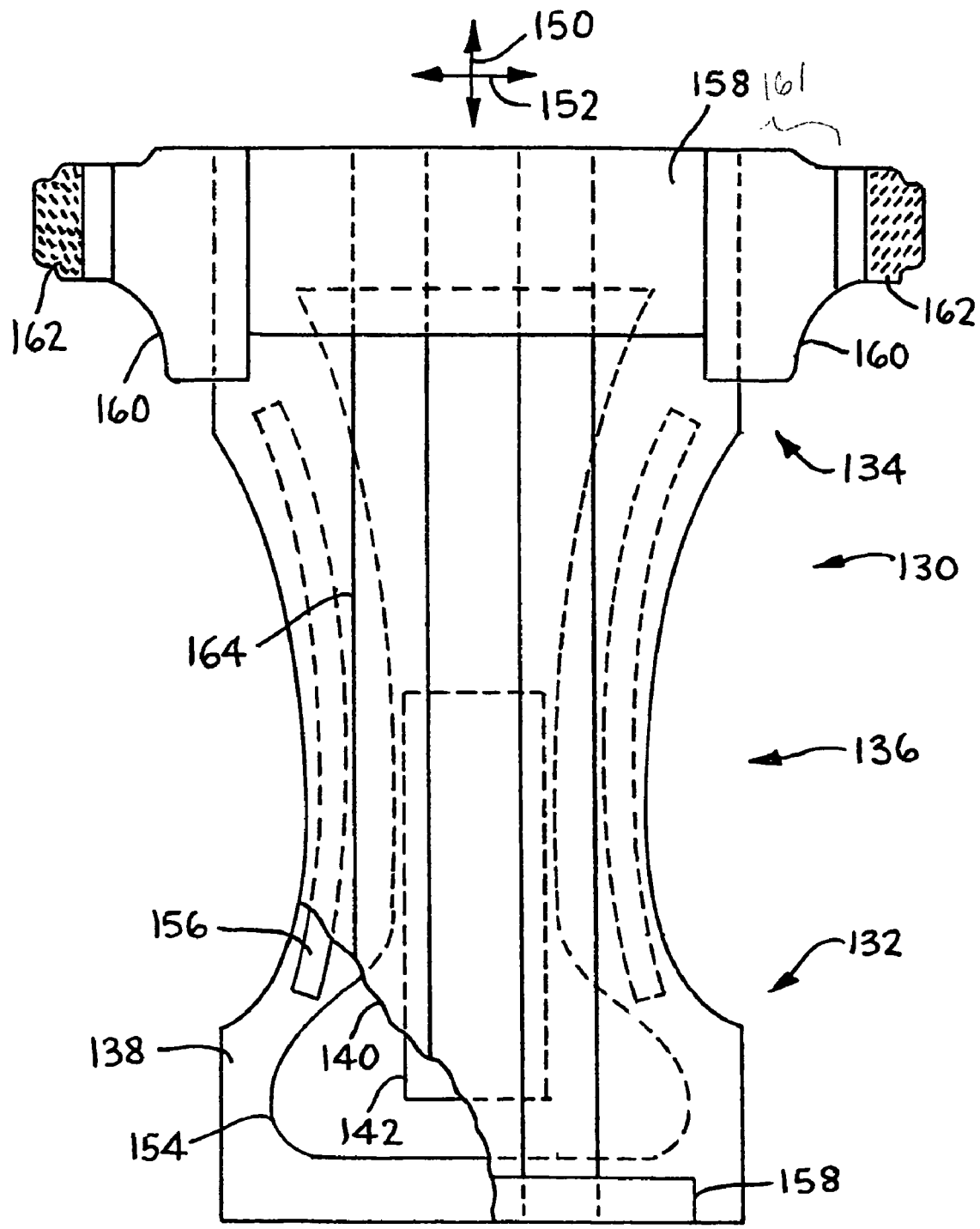
FIG. 4 is an illustration of an exemplary personal care article/product utilizing material made in accordance with the invention.

With reference to FIG. 4, a personal care disposable absorbent product is illustrated which incorporates material made in accordance with the inventive method. In particular, a disposable diaper is illustrated. It should be recognized that any of the previously mentioned personal care products could also incorporate the inventive materials. For example, products such as those described in U.S. Pat. No. 6,702,801 to Van Gompel et al., or U.S. Publication 20040060649 also to Van Gompel may utilize such materials.

The disposable diaper 130 generally defines a front waist section 132, a rear waist section 134, and an intermediate section 136 which interconnects the front and rear waist sections. The front and rear waist sections 132 and 134 include the general portions of the diaper which are constructed to extend substantially over the wearer's front and rear abdominal regions, respectively, during use. The intermediate section 136 of the diaper includes the general portion of the diaper that is constructed to extend through the wearer's crotch region between the legs. Thus, the intermediate section 136 is an area where repeated liquid surges typically occur in the diaper.

The diaper 130 includes, without limitation, an outer cover, or backsheet 138, a liquid permeable bodyside liner, or topsheet, 140 positioned in facing relation with the backsheet 138, and an absorbent core body, or liquid retention structure, 154, such as an absorbent pad, which is located between the backsheet 138 and the topsheet 140. The backsheet 138 defines a length, or longitudinal direction 150, and a width, or lateral direction 152 which, in the illustrated embodiment, coincide with the length and width of the diaper 130. The liquid retention structure 154 generally has a length and width that are less than the length and width of the backsheet 138, respectively. Thus, marginal portions of the diaper 130, such as marginal sections of the backsheet 138, may extend past the terminal edges of the liquid retention structure 154. In the illustrated embodiment, for example, the backsheet 138 extends outwardly beyond the terminal marginal edges of the liquid retention structure 154 to form side margins and end margins of the diaper 130. The topsheet 140 is generally coextensive with the backsheet 138 but may optionally cover an area which is larger or smaller than the area of the backsheet 138, as desired. The outercover can be manufactured from material produced in accordance with the described methods.

To provide improved fit and to help reduce leakage of body exudates from the diaper 130, the diaper side margins and end margins may be elasticized with suitable elastic members, as further explained below. For example, as representatively illustrated in FIG. 4, the diaper 130 may include leg elastics 156 (or leg cuffs) which are constructed to operably tension the side margins of the diaper 130 to provide elasticized leg bands which can closely fit around the legs of the wearer to reduce leakage and provide improved comfort and appearance. Waist elastics 158 are employed to elasticize the end margins of the diaper 130 to provide elasticized waistbands. The waist elastics 158 are configured to provide a resilient, comfortably close fit around the waist of the wearer. The laminates of the inventive methods are suitable for use as the liner if porous or apertured, the backsheet, the leg elastics 156 and the waist elastics 158.

As is known, fastening means, such as hook and loop fasteners may be employed to secure the diaper 130 on a wearer. Alternatively, other fastening means, such as buttons, pins, snaps, adhesive tape fasteners, cohesives, fabric-and-loop fasteners, or the like, may be employed. In the illustrated embodiment, the diaper 130 includes a pair of side panels 160 (or ears) to which the fasteners 162, indicated as the hook portion of a hook and loop fastener, are attached. Generally, the side panels 160 are attached to the side edges of the diaper 130 in one of the waist sections 132, 134 and extend laterally outward therefrom. The side panels 160 may be elasticized or otherwise rendered elastomeric by use of laminate made by the inventive method. For example, the side panels 160, or indeed, any precursor webs of the garment, may be an elastomeric material such as a neck-bonded laminate made in accordance with the inventive method or stretch bonded laminate. Examples of absorbent articles that include elasticized side panels and selectively configured fastener tabs are described in PCT Patent Application No. WO 95/16425 to Roessler; U.S. Pat. No. 5,399,219 to Roessler et al.; U.S. Pat. No. 5,540,796 to Fries; and U.S. Pat. No. 5,595,618 to Fries, each of which is hereby incorporated by reference in its entirety.

The diaper 130 may also include a surge management layer 142, located between the topsheet 140 and the liquid retention structure, to rapidly accept fluid exudates and distribute the fluid exudates to the liquid retention structure 154 within the diaper 130. The diaper 130 may further include a ventilation layer (not illustrated), also called a spacer, or spacer layer, located between the liquid retention structure 154 and the backsheet 138, to insulate the backsheet 138 from the liquid retention structure 154 to reduce the dampness of the garment at the exterior surface of a breathable outer cover, or backsheet, 138. Examples of suitable surge management layers 142 are described in U.S. Pat. No. 5,486,166 to Bishop and U.S. Pat. No. 5,490,846 to Ellis.

As representatively illustrated in FIG. 4, the disposable diaper 130 may also include a pair of containment flaps 164 which are configured to provide a barrier to the lateral flow of body exudates. The containment flaps 164 may be located along the laterally opposed side edges of the diaper 130 adjacent the side edges of the liquid retention structure 154. Each containment flap 164 typically defines an unattached edge which is configured to maintain an upright, perpendicular configuration in at least the intermediate section 136 of the diaper 130, to form a seal against the wearer's body. The containment flaps 164 may extend longitudinally along the entire length of the liquid retention structure 154 or may only extend partially along the length of the liquid retention structure. When the containment flaps 164 are shorter in length than the liquid retention structure 154, the containment flaps 164 can be selectively positioned anywhere along the side edges of the diaper 130 in the intermediate section 136. Such containment flaps 164 are generally well known to those skilled in the art. For example, suitable constructions and arrangements for containment flaps 164 are described in U.S. Pat. No. 4,704,116 to K. Enloe, incorporated by reference herein in its entirety. Such containment flaps may likewise be made from material produced according to the inventive methods.

The diaper 130 may be of various suitable shapes. For example, the diaper may have an overall rectangular shape, T-shape or an approximately hour-glass shape. In the shown embodiment, the diaper 130 has a generally I-shape. Other suitable components which may be incorporated on absorbent articles of the present invention may include waist flaps and the like which are generally known to those skilled in the art. Examples of diaper configurations suitable for use in connection with the instant invention which may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al. and U.S. Pat. No. 5,509,915 to Hanson et al. each of which is hereby incorporated by reference herein in its entirety.

The various components of the diaper 130 are assembled together employing various types of suitable attachment means, such as adhesive, ultrasonic bonds, thermal bonds or combinations thereof. In the shown embodiment, for example, the topsheet 140 and backsheet 138 may be assembled to each other and to the liquid retention structure 154 with lines of adhesive, such as a hot melt, pressure-sensitive adhesive. Similarly, other diaper components, such as the elastic members 156 and 158, fastening members 162, and surge layer 142 may be assembled into the article by employing the above-identified attachment mechanisms.

In a further alternative embodiment, such inventive materials may be particularly useful as a side panel material or backsheet (as previously described) for a diaper or other personal care product. Additionally, such material may be used as an ear attachment substrate, that is, material used in the portion 161 of a personal care article that is used to close the article when worn by a user.

EXAMPLES

The following examples were prepared to analyze/demonstrate the effect of performing the inventive method on known neck bonded laminate material. In particular, neck bonded laminate material was removed from a roll. The neck bonded laminate included two polypropylene spunbond facings of about 0.5 osy (ExxonMobil 3854) which had been point bonded using a wire weave pattern having a level of bonding of between about 14-18 percent. The neck bonded laminate also included a styrenic block copolymer film of about 20 gsm, and in particular of KRATON G 2755 sandwiched between the two facings. The facing materials had been necked from a width of 130 inches to 44 inches or approximately 66 percent neckdown $(((130-44)/130)\times 100)$. The facings were bonded to the film using a thermal lamination process in a nip immediately following film formation.

The sample roll was approximately 10 inches wide. Four 12 inch long samples were removed from the roll. Samples were rotated 90 degrees to make the machine direction of the sample the cross-machine direction (and the cross-machine direction of the sample the machine direction). The rotated sample pieces were taped side by side with 1 inch wide 3M adhesive tape along their original 12 inch dimension (which was the original machine direction of the samples). A necked spunbond leader (feed mechanism) of about 6 feet long was initially attached to the samples to pull the samples through a set of grooved rolls. The samples were then coursed through the set of grooved rolls in a nip with grooves that stretched the samples in the cross-machine direction. Essentially the original machine direction dimension of the samples was now running in the cross-machine direction through the grooved rolls and cross-machine dimension was running in the machine direction through the roll set nip. In this fashion, the samples were stretched in a direction perpendicular to the cross-machine direction of stretch (the original machine direction). This is to model a neck bonded laminate going through a process as shown in FIG. 3.

Each machine oriented groove (such as those described in FIG. 2A) in a 24 inch wide roll set was formed with a depth of 0.200 inch and a peak to peak distance of 0.125 inch, resulting in a maximum draw of about 3.4× (times). In this sample the laminate was coursed through the rolls at a speed thought to be approximately 50 feet per minute and stretched to about 2.6× in the cross machine direction of the nip by adjusting the engagement of the two rolls to about 0.150" at 8 grooves per inch configuration. This means that a 1 inch wide sample would be elongated to about 2.6 inches.

In order to calculate potential draw of the material using the grooved roll apparatus, the potential stretch dimension (such as length) is divided by the original dimension (such as length). If a hypothetical triangle is envisioned wherein the two adjacent peaks of a grooved roll form two of the points and the engagement between the peaks of the different rolls forms the third point of the triangle, the original length may be designated as "P", as the distance between the two adjacent peak points (as seen in FIG. 2a). The distance from the peak (highest point) to the bottom of the engagement peak (lowest point) may be designated as "c" and the depth of engagement may be designated as "E". The stretch length would then be "$2c$", where "c" is the hypotenuse of the right triangle formed from the length P/2, E, and c and, where:

$c=((P/2)^2+E^2)^{1/2}$ so the draw may be expressed by the following equation:

$$\text{Draw} = \frac{2*((P/2)^2 + E^2)^{1/2}}{P}$$

If "P" is equal to 0.125 inches and E is equal to 0.20 inches, the draw would be equal to 3.35. If the penetration was only 0.15 inches instead of 0.20 inches, the draw would be 2.6.

It should be noted that the samples were first run through the rolls at low speed and maximum engagement. The samples did not initially go through and so, the rolls were opened slightly (2 turns) producing a 2.6 draw. The leader was removed so as to eliminate a thicker layer (caused by the tape, spunbond leader and laminate) and the samples were then run through the rolls. The produced samples proved very soft to the touch. The samples were then tested using a cup crush and a drape test, with the control being similarly formulated and constructed laminate samples but without the grooved rolling. Additionally, a cyclic test was run on the various samples. The results of this testing is described in the following Tables 1-4.

Cup Crush and Test Data

TABLE 1

| Sample | Sample # | Cup Crush Load (gf) | Cup Crush Energy (gf mm) | Drape CD (The original material CD) (cm) | Drape MD (The original material MD) (cm) |
|---|---|---|---|---|---|
| Control | 1 | 277 | 4896 | 1.2 | 5.25 |
| Control | 2 | 268 | 6078 | 1.15 | 3.95 |
| Control | 3 | 274 | 5557 | 1.35 | 5.45 |
| Control | 4 | 221 | 4627 | 1.25 | 5.75 |
| Control | 5 | 257 | 4688 | 1.25 | 5.1 |
| Avg. | | 259 | 5169 | 1.24 | 5.1 |
| Std. Dev. | | 23 | 628 | 0.074 | 0.687 |
| Test Sample | 1 | 141 | 2526 | 1.45 | 2.2 |
| Test Sample | 2 | 126 | 2149 | 1.35 | 2.35 |
| Test Sample | 3 | 111 | 1789 | 1.3 | 2.6 |
| Avg. | | 126 | 2155 | 1.367 | 2.383 |
| Std. Dev. | | 15 | 369 | 0.076 | 0.202 |

Note that gf is grams force.
The cup crush values have been rounded to a significant number (following averaging and other calculations).

Table 2

Cup Crush Data was normalized to the material basis weight of 92.4 gsm. The normalized value was obtained by weighing the control and test samples (3 samples, each being 3 by 6 inches (for a total of 54 sq. inches)), and converted to gsm. The three control samples weighed a total of 3.24 grams, and the three test samples weighed a total of 3.21 g. The rounded values (above) for cup crush were then divided by the total basis weight of 92.4 gsm for each sample for load or peak energy. This figure then was rounded to the significant number place unit.

TABLE 2

| Sample | Sample # | Cup Crush Load Normalized Units (gf/gsm) | Cup Crush Energy Normalized Units (gf mm/gsm) |
|---|---|---|---|
| Control | 1 | 3.0 | 53 |
| Control | 2 | 2.0 | 66 |
| Control | 3 | 3.0 | 60 |
| Control | 4 | 2.4 | 50 |
| Control | 5 | 2.8 | 51 |
| Avg. | | 2.82 +/− 0.25 | 56 +/− 7 |
| Test Sample | 1 | 1.5 | 27 |
| Test Sample | 2 | 1.4 | 23 |
| Test Sample | 3 | 1.2 | 19 |
| Avg. | | 1.4 +/− 0.15 | 23 +/− 4 |

As can be seen from the above Tables, the process of stretching the laminate material in a direction perpendicular to the direction of elasticity softens the overall material as measured by the cup crush load test. Therefore, in one embodiment, the cup crush load value and cup crush energy value is less for a material stretched in accordance with the method than for the same material not stretched in accordance with the method. In still a further alternative embodiment of the inventive method, the produced material demonstrates a cup crush load value of between about 100 to 150 gf. In still a further alternative embodiment of the inventive method, the produced material demonstrates a cup crush load value of between about 40 and 65 percent of a similar laminate material that has not gone through the production method. In still a further alternative embodiment of the inventive method, the produced material demonstrates a normalized cup crush load value of between about 1-2 gf/gsm. In one embodiment, the method produces a material with a cup crush test value for load normalized by a basis weight, of less than about 2 gf/gsm. Desirably such cup crush test is at least about 50 percent less than the value for the same material without such treatment.

In still a further alternative embodiment of the inventive method, the produced material demonstrates a cup crush energy of between about 1700 and 2500 gf-mm. In still a further alternative embodiment of the inventive method, the produced material demonstrates a normalized cup crush energy of between about 20 and 30 gf-mm. In yet a further alternative embodiment of the inventive method, the produced material demonstrates a cup crush energy of between about 30 and 55 percent of a similar material that has not been produced by the inventive method.

In yet still a further alternative embodiment of the inventive method, the material produced (with original cross-machine direction elasticity) demonstrates a machine-direction drape value of between about 2 and 3 cm. In still a further alternative embodiment of the inventive method, the material produced demonstrates a drape value in the direction perpendicular to the original direction of elasticity, of between about 35 and 65 percent of a similar material that has not been produced in accordance with the inventive method. In another embodiment, the drape value of the material (following treatment by the inventive method) in the direction perpendicular to the direction of original elasticity of the material, is reduced by at least about 35 percent, over similar materials without such treatment. In a further alternative embodiment, the drape value is reduced by at least 50 percent over such materials that have not been stretched.

Similar laminate material samples from the same neck bonded laminate roll were later evaluated for behavior in a cycle test using the above described procedure. The results of such testing are reflected in the following Table 3. These values are in the original CD, meaning the direction in which such materials are elastic.

TABLE 3

| Sample Descr. | Load $1^{st}$ 30% Up (g) | Load @ $1^{st}$ Ext. (g) | Load $1^{st}$ 30% Down (g) | Load $2^{nd}$ 30% Down (g) | Percent Set (%) | Elg. @$1^{st}$ 2K | Elg.@ Stop Ld. (%) | Peak Ld. (g) | Elg.@ Peak |
|---|---|---|---|---|---|---|---|---|---|
| Test Specimen 1 | 501 | 831 | 110 | 100 | 15 | Not Dete. | Not Dete. | 1979 | 264 |
| Test Specimen 2 | 470 | 788 | 99 | 90 | 16 | Not Dete. | Not Dete. | 1794 | 248 |
| Test Specimen 3 | 509 | 838 | 105 | 96 | 15 | Not Dete. | 254 | 2039 | 272 |
| Control 1 | 534 | 812 | 63 | 55 | 21 | Not Dete. | 183 | 3229 | 248 |
| Control 2 | 570 | 852 | 87 | 78 | 18 | Not Dete. | 199 | 3143 | 270 |
| Control 3 | 513 | 779 | 60 | 53 | 21 | Not Dete. | 187 | 3276 | 259 |

The values have been rounded to the first significant place unit.

Stress/strain curves were created from the data generated and the image was enlarged 200 or 400 percent. The graphs were reviewed to mechanically determine the energy placed into the sample during stretching and the energy recovered following retraction. The following values were determined, as reflected in Table 4 below.

TABLE 4

| Sample | Energy in (gf-mm) | Energy recovered (gf-mm) | % Energy Recovered |
|---|---|---|---|
| Test Specimen 1 | 0.50 + 0.325 | 0.325 | 39.4 |
| Test Specimen 2 | 0.879 + 0.583 | 0.583 | 39.9 |
| Test Specimen 3 | 0.587 + 0.398 | 0.398 | 40.4 |
| Control 1 | 1.369 + 0.607 | 0.607 | 30.7 |
| Control 2 | 1.275 + 0.578 | 0.578 | 31.1 |
| Control 3 | 1.392 + 0.694 | 0.694 | 33.3 |

The average values of these three test specimens and three control samples were reduced into a summary Table 5 below.

TABLE 5

| Test | Test Material Avg. | Test Material Std. Dev. | Control Material Avg. | Control Material Std. Dev. |
|---|---|---|---|---|
| 30% Up, $1^{st}$ (grams) | 493 | 20 | 539 | 29 |
| 100% Up, $1^{st}$ (grams) | 819 | 27 | 814 | 37 |
| 30% Down, $1^{st}$ (grams) | 105 | 5 | 70 | 15 |
| 30% Down $2^{nd}$ (grams) | 95.5 | 5.3 | 61.8 | 13.7 |
| Percent Set | 15.1 | 0.6 | 20.1 | 1.9 |
| Peak Load (grams) | 1940 | 130 | 3216 | 70 |
| % Elongation @ PEAK LOAD | 260 | 14 | 259 | 11 |
| Percent Energy Recovered | 39.9 | 0.5 | 31.5 | 1.6 |

As can be seen from the data, the percent set is noticeably reduced following such treatment. The test variability of a sample is also an important factor to making an inexpensive, consistent and high performance product. In the cases above the test variability varies significantly between the test and control products. For example, the coefficient of variability is (5/105) or 4.7 percent versus (15/70) or 21 percent for 30% Down, 1st results. Similar significant results apply to 30% Down 2nd results and percent set results. As can be seen from the data, the coefficient of variation was significantly reduced. The coefficient of variability reduced by 78 percent for the first 30 percent Down (test material vs. control material), 75 percent for the second 30 percent Down (test material vs. control material), and 58 percent for the set values (test material vs. control material).

Although various embodiments of the invention have been described using specific terms, devices, and methods, such description is for illustrative purposes only. The words are words of description rather than of limitation. It should be recognized that all patents and applications described herein are hereby incorporated by reference in their entirety. It is to be further understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A method for producing a single direction elastic laminate comprising the steps of:
   a. providing a one direction elastic laminate material including at least one elastic layer and one facing layer comprising a nonwoven web of fibers and having a single direction of elasticity;
   b. coursing said one direction elastic laminate material through at least one stretching apparatus, such that said stretching apparatus stretches the laminate material in a direction perpendicular to the single direction of elasticity of the elastic laminate material, thereby producing a material that is extended in a direction perpendicular to the direction of elasticity and also demonstrates enhanced elastic performance in the single direction of elasticity.

2. The method of claim 1 wherein said one direction elastic laminate material is either a necked bonded laminate or a stretch bonded laminate.

3. The method of claim 1 wherein said stretching apparatus is selected from the group consisting of intermeshing grooved rolls, intermeshing discs on axles, belts and tenter frames.

4. The method of claim 1 further comprising the step of stretching said elastic laminate material through two sets of stretching apparatus, such that said laminate material is stretched both in a direction perpendicular to the single direction of elasticity and also in a direction parallel to the single direction of elasticity.

5. The method of claim 1, wherein said elastic laminate material is a pre-formed material.

6. The method of claim 1 wherein said produced material demonstrates enhanced elastic performance in a direction perpendicular to the single direction of elasticity.

7. A method for producing a cross-machine direction elastic laminate comprising the steps of:
   a. providing a neck bonded laminate material including at least one elastic layer and one facing layer comprising a nonwoven web of fibers and having a cross-machine direction of elasticity;
   b. coursing said neck bonded laminate material through at least one stretching apparatus, such that said stretching apparatus stretches the laminate material in the machine direction, thereby producing a material that is extended in the machine direction and also demonstrates enhanced elastic performance in the cross-machine direction.

8. The method of claim 7, wherein said stretching apparatus is at least one set of intermeshing grooved rolls.

9. The method of claim 8, wherein said neck bonded laminate material is coursed between two stretching apparatus.

10. The method of claim 9, wherein each of said stretching apparatus stretch said laminate in non-parallel directions.

11. The method of claim 7, wherein said elastic layer is either a film, a nonwoven sheet, a foam sheet, scrim or a combination thereof.

12. The method of claim 11 wherein said produced material demonstrates enhanced elastic performance in the machine direction.

13. The method of claim 7, wherein said laminate is a pre-formed material.

14. A method for producing a machine direction elastic laminate comprising the steps of:
   a. providing a stretch bonded laminate material including at least one elastic layer and one facing layer comprising a nonwoven web of fibers and having machine direction elasticity;
   b. coursing said stretch bonded laminate material through at least one stretching apparatus, such that said stretching apparatus stretches the laminate material in the cross machine direction, thereby producing a material that is extended in the cross-machine direction and also demonstrates enhanced elastic performance in the machine direction.

15. The method of claim 14, wherein said elastic layer is selected from the group consisting of a nonwoven web, a film, an array of parallel filaments, a scrim, a foam sheet and a combination thereof.

16. The method of claim 14, wherein said elastic layer is selected from the group consisting of a nonwoven web, a film, a scrim, a foam sheat and a combination thereof.

17. The method of claim 14 wherein said stretching apparatus is selected from the group consisting of intermeshing grooved rolls, intermeshing discs on axles, tenter frames, and belt arrangements.

18. The method of claim 14 wherein said laminate is coursed through two stretching apparatus.

19. The method of claim 18, wherein each of said stretching apparatus stretch said laminate in non-parallel directions.

20. The method of claim 16 wherein said produced material also demonstrates enhanced elastic performance in the cross-machine direction.

21. The method of claim 14, wherein said laminate is a pre-formed material.

* * * * *

UNITED STATES PATENT AND TRADEMARK OFFICE
CERTIFICATE OF CORRECTION

PATENT NO. : 7,651,653 B2  Page 1 of 1
APPLICATION NO. : 11/020970
DATED : January 26, 2010
INVENTOR(S) : Morman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1189 days.

Signed and Sealed this

Twenty-third Day of November, 2010

David J. Kappos
*Director of the United States Patent and Trademark Office*